United States Patent
Makino

(10) Patent No.: US 12,022,991 B2
(45) Date of Patent: Jul. 2, 2024

(54) ENDOSCOPE PROCESSOR, INFORMATION PROCESSING DEVICE, AND PROGRAM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 674 days.

(21) Appl. No.: 17/267,686

(22) PCT Filed: Mar. 11, 2020

(86) PCT No.: PCT/JP2020/010409
§ 371 (c)(1),
(2) Date: Feb. 10, 2021

(87) PCT Pub. No.: WO2020/195807
PCT Pub. Date: Oct. 1, 2020

(65) Prior Publication Data
US 2021/0161363 A1   Jun. 3, 2021

(30) Foreign Application Priority Data

Mar. 27, 2019   (JP) ................... 2019-061432

(51) Int. Cl.
*A61B 1/00* (2006.01)
*G06N 3/08* (2023.01)

(52) U.S. Cl.
CPC .. *A61B 1/000094* (2022.02); *A61B 1/000096* (2022.02); *A61B 1/0005* (2013.01); *G06N 3/08* (2013.01)

(58) Field of Classification Search
CPC ........ A61B 1/000094; A61B 1/000096; A61B 1/0005; G06N 3/08
(Continued)

(56) References Cited

U.S. PATENT DOCUMENTS 5,754,676 A      5/1998  Komiya et al.
11,559,298 B2 *  1/2023  Scheib ............... G01B 11/2513
(Continued)

FOREIGN PATENT DOCUMENTS

JP     7-284090     10/1995
JP     2010-512173  4/2010
(Continued)

OTHER PUBLICATIONS

Official Communication issued in International Bureau of WIPO Patent Application No. PCT/JP2020/010409, dated May 19, 2020.
(Continued)

*Primary Examiner* — Gabriel I Garcia
(74) *Attorney, Agent, or Firm* — GREENBLUM & BERNSTEIN, P.L.C.

(57) ABSTRACT

An endoscope processor or the like is provided which has a high ability to detect lesions. The endoscope processor includes an image acquisition unit that acquires a captured image taken by an endoscope, a first image processing unit that generates a first processed image based on the captured image acquired by the image acquisition unit, a second image processing unit that generates a second processed image based on the captured image, and an output unit that outputs an acquired disease status using a learning model, which outputs a disease status, when the first processed image generated by the first image processing unit and the second processed image generated by the second image processing unit are input.

19 Claims, 23 Drawing Sheets

(58) Field of Classification Search
USPC .......................................................... 382/128
See application file for complete search history.

(56) References Cited

U.S. PATENT DOCUMENTS

| | | | |
|---|---|---|---|
| 11,599,998 B2* | 3/2023 | Fan | G16H 50/20 |
| 2016/0350914 A1 | 12/2016 | Champlin et al. | |
| 2017/0004625 A1 | 1/2017 | Kamiyama et al. | |
| 2018/0070798 A1 | 3/2018 | Kamiyama et al. | |
| 2018/0150675 A1 | 5/2018 | Kamiyama et al. | |
| 2018/0247153 A1 | 8/2018 | Ganapati et al. | |
| 2018/0279866 A1 | 10/2018 | Makino | |
| 2018/0296281 A1 | 10/2018 | Yeung et al. | |
| 2019/0034800 A1* | 1/2019 | Shiratani | G06N 3/042 |
| 2019/0311475 A1 | 10/2019 | Hosoi | |
| 2021/0113075 A1 | 4/2021 | Ito et al. | |
| 2021/0150277 A1* | 5/2021 | Kamon | G06V 10/82 |

FOREIGN PATENT DOCUMENTS

| | | |
|---|---|---|
| JP | 2015-181594 | 10/2015 |
| JP | 2018-517209 | 6/2018 |
| WO | 2008/024419 | 2/2008 |
| WO | 2016/185617 | 11/2016 |
| WO | 2017/017722 | 2/2017 |
| WO | 2017/057680 | 4/2017 |
| WO | 2017/175282 | 10/2017 |
| WO | 2018/008593 | 1/2018 |
| WO | 2018/160288 | 9/2018 |
| WO | 2018/188466 | 10/2018 |
| WO | 2020/012563 | 1/2020 |

OTHER PUBLICATIONS

Jun. 19, 2023 Japanese Office Action issued in counterpart Japanese patent application No. 2019-061432 and English translation thereof.
May 19, 2023 Chinese Office Action in corresponding Chinese Application No. 202080004454.X and partial machine translation thereof.
Apr. 9, 2024 Japanese Office Action in corresponding Japanese Application No. JP 2019-061432 and English translation thereof.

* cited by examiner

| ORIGINAL IMAGE | DISEASE | | | IMAGE PROCESSING | | | |
|---|---|---|---|---|---|---|---|
| | PART | ULCER | TUMOR | BLEEDING | FIRST PROCESSED IMAGE | SECOND PROCESSED IMAGE | THIRD PROCESSED IMAGE | FOURTH PROCESSED IMAGE |

| ORIGINAL IMAGE | PART | ULCER | TUMOR | BLEEDING | FIRST PROCESSED IMAGE | SECOND PROCESSED IMAGE | THIRD PROCESSED IMAGE | FOURTH PROCESSED IMAGE | |
|---|---|---|---|---|---|---|---|---|---|
| A0011.bmp | STOMACH | SEVERE | NONE | PRESENT | A0011-1.bmp | A0011-2.bmp | A0011-3.bmp | A0011-4.bmp | ... |
| A0012.bmp | STOMACH | MILD | MALIGNANT | NONE | A0012-1.bmp | A0012-2.bmp | A0012-3.bmp | A0012-4.bmp | ... |
| A0013.bmp | STOMACH | NORMAL | NONE | NONE | A0013-1.bmp | A0013-2.bmp | A0013-3.bmp | A0013-4.bmp | ... |
| A0014.bmp | STOMACH | MODERATE | BENIGN | NONE | A0014-1.bmp | A0014-2.bmp | A0014-3.bmp | A0014-4.bmp | ... |
| A0015.bmp | STOMACH | MODERATE | BENIGN | NONE | A0015-1.bmp | A0015-2.bmp | A0015-3.bmp | A0015-4.bmp | ... |

FIG. 9

| LEARNING MODEL ID | PART | DISEASE | INPUT DATA |
|---|---|---|---|
| model01 | STOMACH | ULCER | FIRST PROCESSED IMAGE, SECOND PROCESSED IMAGE, THIRD PROCESSED IMAGE |
| model02 | STOMACH | TUMOR | THIRD PROCESSED IMAGE, FOURTH PROCESSED IMAGE |
| model03 | LARGE INTESTINE | ULCER | FIRST PROCESSED IMAGE, SECOND PROCESSED IMAGE, FIFTH PROCESSED IMAGE |
| model04 | LARGE INTESTINE | TUMOR | THIRD PROCESSED IMAGE, FOURTH PROCESSED IMAGE, SIXTH PROCESSED IMAGE |

FIG. 15

| LEARNING MODEL ID | PART | DISEASE | INPUT DATA | | | | | | |
|---|---|---|---|---|---|---|---|---|---|
| | | | FIRST PROCESSED IMAGE | SECOND PROCESSED IMAGE | THIRD PROCESSED IMAGE | FOURTH PROCESSED IMAGE | FIFTH PROCESSED IMAGE | SIXTH PROCESSED IMAGE | |
| model101 | STOMACH | ULCER | 1 | 1 | 1 | 1 | 1 | 1 | ... |
| model102 | STOMACH | ULCER | 0 | 1 | 1 | 1 | 1 | 1 | ... |
| model103 | STOMACH | ULCER | 0 | 0 | 1 | 1 | 1 | 1 | ... |
| model104 | STOMACH | ULCER | 0 | 0 | 0 | 1 | 1 | 1 | ... |
| model105 | STOMACH | ULCER | 0 | 0 | 0 | 0 | 1 | 1 | ... |
| model106 | STOMACH | ULCER | 0 | 0 | 0 | 0 | 0 | 1 | ... |

FIG. 18

| ORIGINAL IMAGE | PART | DISEASE | INPUT DATA | | | | | DETERMINATION RESULT |
|---|---|---|---|---|---|---|---|---|
| | | | FIRST PROCESSED IMAGE | SECOND PROCESSED IMAGE | THIRD PROCESSED IMAGE | FOURTH PROCESSED IMAGE | ...... | |
| B0111.bmp | STOMACH | ULCER | 1 | 0 | 0 | 1 | ...... | SEVERE |
| B0111.bmp | STOMACH | TUMOR | 0 | 0 | 1 | 0 | ...... | NONE |
| B0111.bmp | STOMACH | BLEEDING | 1 | 1 | 0 | 0 | ...... | NONE |
| B0112.bmp | STOMACH | ULCER | 0 | 1 | 0 | 1 | ...... | MILD |
| B0112.bmp | STOMACH | TUMOR | 1 | 0 | 0 | 0 | ...... | BENIGN |
| B0112.bmp | STOMACH | BLEEDING | 1 | 0 | 0 | 1 | ...... | PRESENT |

| ENDOSCOPE IMAGE | PART | SCORE | |
|---|---|---|---|
| | | REDNESS | VASCULAR SEE-THROUGH |
| A0051.bmp | STOMACH | 100 | 10 |
| A0052.bmp | STOMACH | 20 | 100 |
| A0053.bmp | STOMACH | 50 | 20 |
| A0054.bmp | STOMACH | 80 | 0 |
| A0055.bmp | STOMACH | 0 | 40 |

ENDOSCOPE PROCESSOR, INFORMATION PROCESSING DEVICE, AND PROGRAM

TECHNICAL FIELD

The present invention relates to an endoscope processor, an information processing device, a program, an information processing method, and a method of generating a learning model.

BACKGROUND ART

Computer-aided diagnostic technology has been developed which automatically detects lesions using a learning model from medical images such as endoscope images. A method of generating a learning model by supervised machine learning using training data with a correct answer label is known.

A learning method is proposed which combines a first learning using an image group taken by a normal endoscope as the training data and a second learning using an image group taken by a capsule endoscope as the training data (Patent Literature 1).

CITATION LIST

Patent Literature

Patent Literature 1: WO 2017/175282 A

SUMMARY OF INVENTION

Technical Problem

However, the method of Patent Literature 1 has a problem that the ability to detect a lesion is not sufficient.

In one aspect, it is an object of the invention to provide an endoscope processor or the like which has a high ability to detect a lesion.

Solution to Problem

An endoscope processor includes an image acquisition unit that acquires a captured image taken by an endoscope, a first image processing unit that generates a first processed image based on the captured image acquired by the image acquisition unit, a second image processing unit that generates a second processed image based on the captured image, and an output unit that outputs an acquired disease status using a learning model, which outputs a disease status, when the first processed image generated by the first image processing unit and the second processed image generated by the second image processing unit are input.

Advantageous Effects of Invention

In one aspect, it is possible to provide an endoscope processor or the like having a high ability to detect a lesion.

BRIEF DESCRIPTION OF DRAWINGS

FIG. 8 is an explanatory diagram for explaining a record layout of a training data DB.

FIG. 9 is an explanatory diagram for explaining a record layout of a learning model DB.

FIG. 15 is an explanatory diagram for explaining a record layout of a learning model DB of a fourth embodiment.

FIG. 18 is an explanatory diagram for explaining a record layout of an additional training data DB according to a fifth embodiment.

DESCRIPTION OF EMBODIMENTS

First Embodiment

Figure 1:
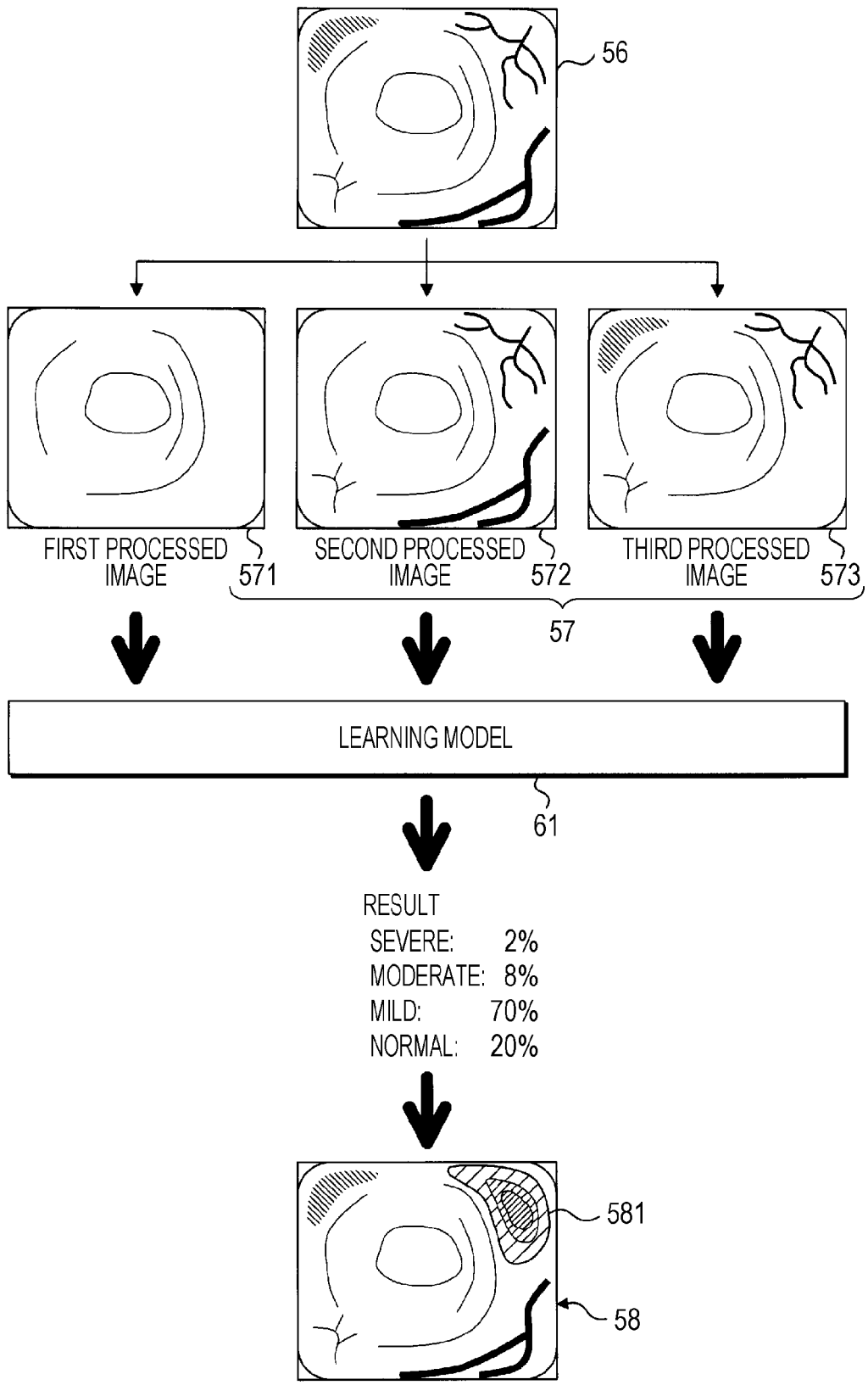
FIG. 1 is an explanatory diagram for explaining an outline of an endoscope system using a learning model.

FIG. 1 is an explanatory diagram for explaining an outline of an endoscope system 10 using a learning model 61. An original image 56 taken with an endoscope 40 (see FIG. 3) is subjected to different image processing so as to generate a processed images 57 such as a first processed image 571, a second processed image 572, and a third processed image 573.

In FIG. 1, a case where three processed images 57 are generated and used will be described as an example, but the number of processed images 57 may be two or four or more.

Any of the processed images 57 may be the same image as the original image 56, that is, an image in which the original image 56 is not subjected to image processing.

The original image 56 may be a captured image taken by an image sensor provided at a distal tip 443 (see FIG. 3) of the endoscope 40 and transmitted to an endoscope processor 20 (see FIG. 3), or an endoscope image 59 (see FIG. 5) which is obtained by subjecting the captured image to various image processing such as gamma correction, white balance correction, and shading correction in the endoscope processor 20 to be made easy for a user to see. The original image 56 may be an image in the middle of generating the endoscope image 59 from the captured image. Since the process of generating the endoscope image 59 from the captured image has been performed conventionally, the detailed description thereof will be omitted.

The first processed image 571, the second processed image 572, and the third processed image 573 are input to the learning model 61. A disease status is output from the learning model 61. The details of the learning model 61 will be described later.

In this embodiment, the case where the disease status is the severity of the ulcer will be described as an example. It is determined that the region shown in the original image 56 has a 2% probability of having a severe ulcer, an 8% probability of having a moderate ulcer, a 70% probability of having a mild ulcer, and a 20% change of no ulcer.

For example, a first interest region 581 is extracted by a model visualization method such as Grad-CAM (Gradient-weighted Class Activation Mapping), Grad-CAM++, or the like. The first interest region 581 is a region in the processed image 57 input to the learning model 61 that strongly affects the output. In the lower part of FIG. 1, an example of an interest region image 58 showing an index indicating the range of the first interest region 581 is illustrated. In the example illustrated in FIG. 1, the interest region image 58 is an image in which the first interest region 581 is superimposed on the endoscope image 59. The first interest region 581 is displayed using finer hatching as the degree of influence on the output is higher.

The first interest region 581 may be expressed in a so-called heat map format in which the degree of influence is expressed by hue. In the first interest region 581, the degree of influence may be represented by contour lines. The interest region image 58 may be displayed by superimposing the first interest region 581 on a plain image such as white or black.

The first interest region 581 can be extracted from each processed image 57 input to the learning model 61, and calculated by adding the degree of influence in each processed image 57. The first interest region 581 may be extracted from a part of the processed images 57 input to the learning model 61.

In the image processing for generating the endoscope image 59 from the captured image, an image is generated so that the user can easily find a lesion visually. However, when the image processing is performed with an emphasis on visibility by the user, a part of the information contained in the captured image becomes inconspicuous.

With the use of the plurality of processed images 57, it is possible to input an image emphasizing such inconspicuous information into the learning model 61. The learning model 61 outputs the disease status by utilizing the feature that the information becomes inconspicuous in the endoscope image 59. From the above, it is possible to provide the endoscope processor 20 or the like having a high ability to detect a lesion.

Figure 2:
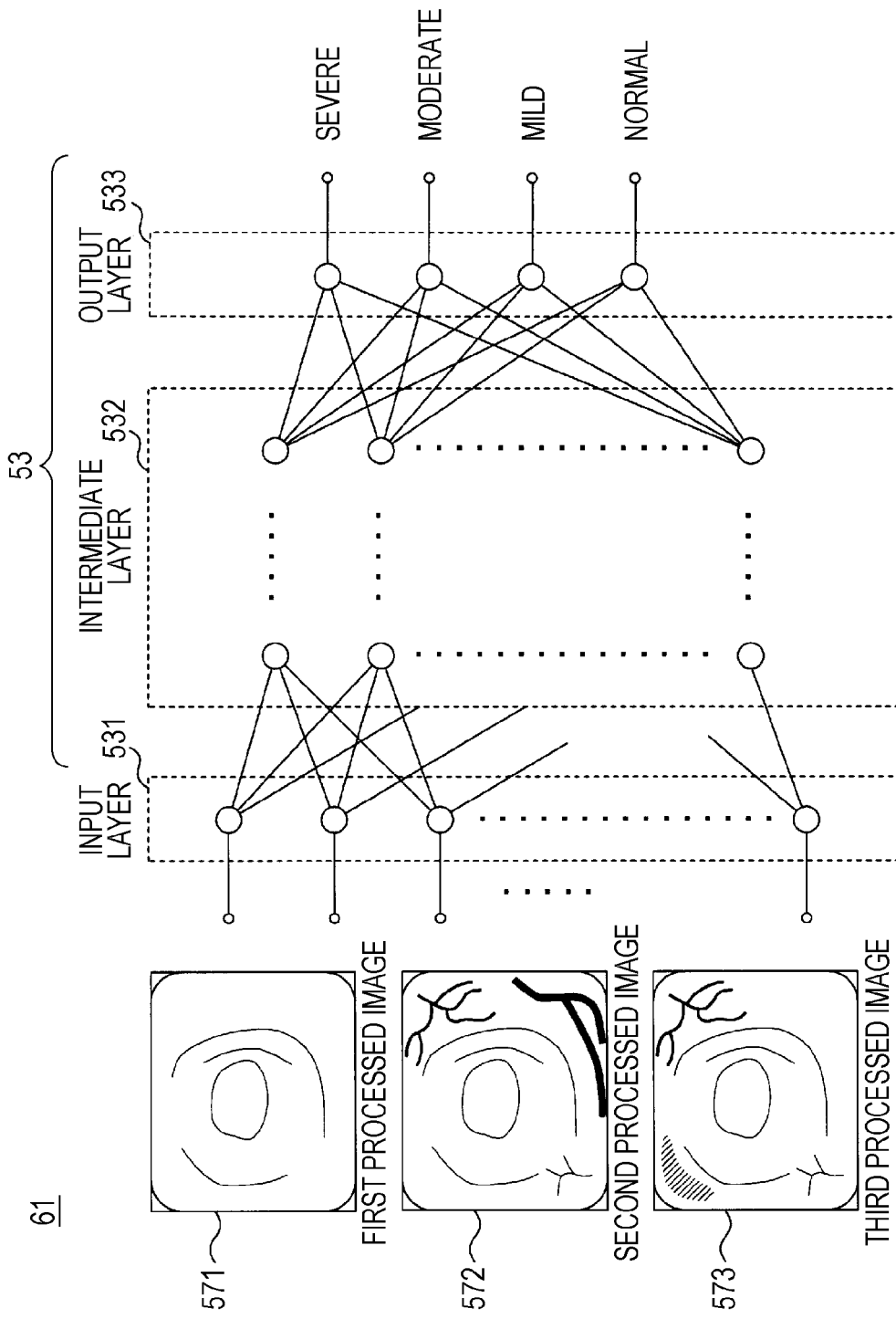
FIG. 2 is an explanatory diagram for explaining the configuration of the learning model.

FIG. 2 is an explanatory diagram for explaining the configuration of the learning model 61. The learning model 61 outputs the disease status shown in the original image 56 when the three processed images 57 of the first processed image 571, the second processed image 572, and the third processed image 573 are input.

The learning model 61 of this embodiment performs learning using CNN. Each model is configured by an input layer 531, an intermediate layer 532, an output layer 533, and a neural network model 53 having a convolution layer and a pooling layer (not illustrated).

Three processed images 57 of the first processed image 571, the second processed image 572, and the third processed image 573 are input to the learning model 61. The input image is repeatedly processed by the convolution layer and the pooling layer, and then input to the fully-connected layer.

The probability of the disease status is output to the output layer 533. In FIG. 2, the output layer 533 has four output nodes for outputting a probability of having severe ulcers, a probability of having moderate ulcers, a probability of having mild ulcers, and a probability of having no ulcers in the region shown in the original image 56.

Figure 7:
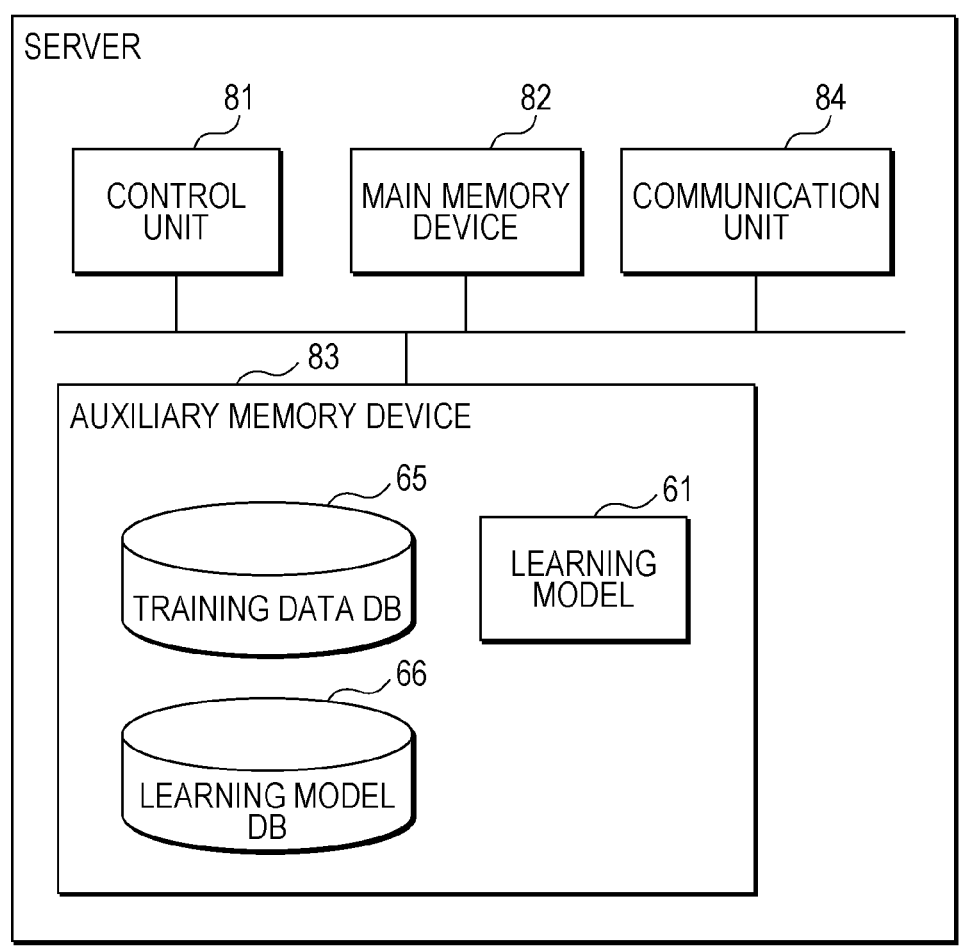
FIG. 7 is an explanatory diagram for explaining the configuration of a server.

The parameter of each neuron in the intermediate layer 532 is adjusted by machine learning based on the training data DB (Database) 65 (see FIG. 7). The training data DB 65 will be described later.

The learning model 61 is generated for each disease to be diagnosed and includes input nodes and output nodes which are different in number for each disease. For example, the learning model 61 is further generated for each part to be diagnosed for a disease such as cancer and ulcer that occurs in many parts.

Table 1 shows an example of image processing that generates the processed image 57 from the original image 56.

TABLE 1

| No. | Processing content |
| --- | --- |
| 1 | R component emphasis |
| 2 | G component emphasis |
| 3 | B component emphasis |
| 4 | R component extraction |
| 5 | G component extraction |
| 6 | B component extraction |
| 7 | R component removal |
| 8 | G component removal |
| 9 | B component removal |
| 10 | Edge emphasis |
| 11 | Normal image |
| 12 | Edge emphasis after R component emphasis |

Generally, each pixel constituting a color image has three color components of RGB (Red, Green, Blue). No. 1 in Table 1 shows a process of emphasizing the R component of each pixel of the original image 56. Specifically, for example, the G component and the B component of each pixel are reduced to half from the original image 56, so that the R component is relatively emphasized. Similarly, No. 2 shows a process of emphasizing the G component, and No. 3 shows a process of emphasizing the B component.

No. 4 shows a process of extracting only the R component of each pixel of the original image 56, that is, a process of making the G component and the B component of each pixel zero. Similarly, No. 5 shows a process of extracting only the G component, and No. 6 shows a process of extracting only the B component.

No. 7 shows a process of removing only the R component of each pixel of the original image 56, that is, a process of making the R component of each pixel zero. Similarly, No. 8 shows a process of removing only the G component, and No. 9 shows a process of removing only the B component.

No. 10 means a process of applying an edge emphasizing filter to the original image 56 to emphasize the edge component. No. 11 means a series of image processing that generates the endoscope image 59 that is made easy for the user to see. When the original image 56 is the endoscope image 59, No. 11 means that the original image 56 is not subjected to image processing.

Table 1 shows an example of an image processing method, and the processed image 57 can be generated by using any other image processing method. For example, No. 12 in Table 1 is a process in which the R component emphasizing process of No. 1 is performed and then the edge emphasizing process of No. 10 is performed. In addition, the processed image 57 may be generated by combining a plurality of processes in any order. A unique number is assigned to each combination as in No. 12.

By using the processed image 57 that has undergone these image processing as an input, it is possible to realize the learning model 61 that detects a disease that has not been able to be extracted from the endoscope image 59 or the captured image.

Since all of the image processing illustrated in Table 1 apply less load on the control unit 21 (see FIG. 4), the plurality of processed images 57 can be generated in real time.

Figure 3:
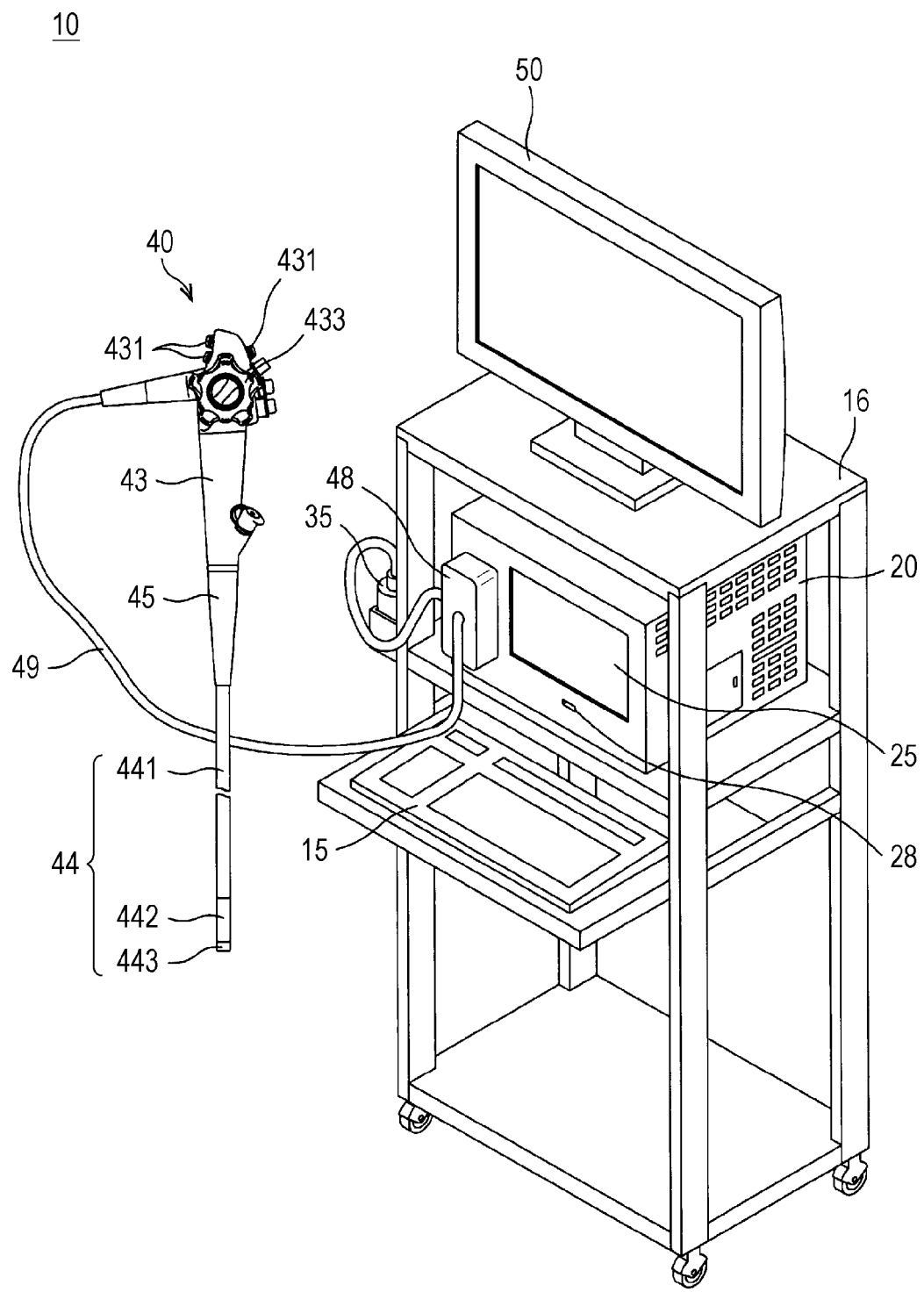
FIG. 3 is an explanatory diagram illustrating the appearance of the endoscope system.

FIG. 3 is an explanatory diagram illustrating the appearance of the endoscope system 10. The endoscope system 10 includes the endoscope processor 20, the endoscope 40, and a display device 50. The display device 50 is, for example, a liquid crystal display device or an organic EL (Electro Luminescence) display device.

The display device 50 is installed on the upper stage of a storage shelf 16 with casters. The endoscope processor 20 is housed in the middle stage of the storage shelf 16. The storage shelf 16 is arranged in the vicinity of an endoscopic examination bed (not illustrated). The storage shelf 16 includes a pull-out shelf on which a keyboard 15 connected to the endoscope processor 20 is mounted.

The endoscope processor 20 has a substantially rectangular parallelepiped shape and is provided with a touch panel 25 on one surface. A reading portion 28 is arranged at the bottom of the touch panel 25. The reading portion 28 is a connection interface for reading and writing a portable recording medium such as a USB connector, an SD (Secure Digital) card slot, or a CD-ROM (Compact Disc Read Only Memory) drive.

The endoscope 40 includes an insertion portion 44, an operation unit 43, a universal cord 49, and a scope connector 48. The operation unit 43 is provided with a control button 431. The insertion portion 44 is long, and has one end connected to the operation unit 43 via a bend preventing portion 45. The insertion portion 44 includes a soft portion 441, a bending portion 442, and a distal tip 443 in the order from the operation unit 43 side. The bending portion 442 is bent according to an operation of a bending knob 433.

The universal cord 49 is long, and has a first end connected to the operation unit 43 and a second end connected to the scope connector 48. The universal cord 49 is soft. The scope connector 48 has a substantially rectangular parallelepiped shape. The scope connector 48 is provided with an air/water supply port 36 (see FIG. 4) for connecting an air/water supply tube.

Figure 4:
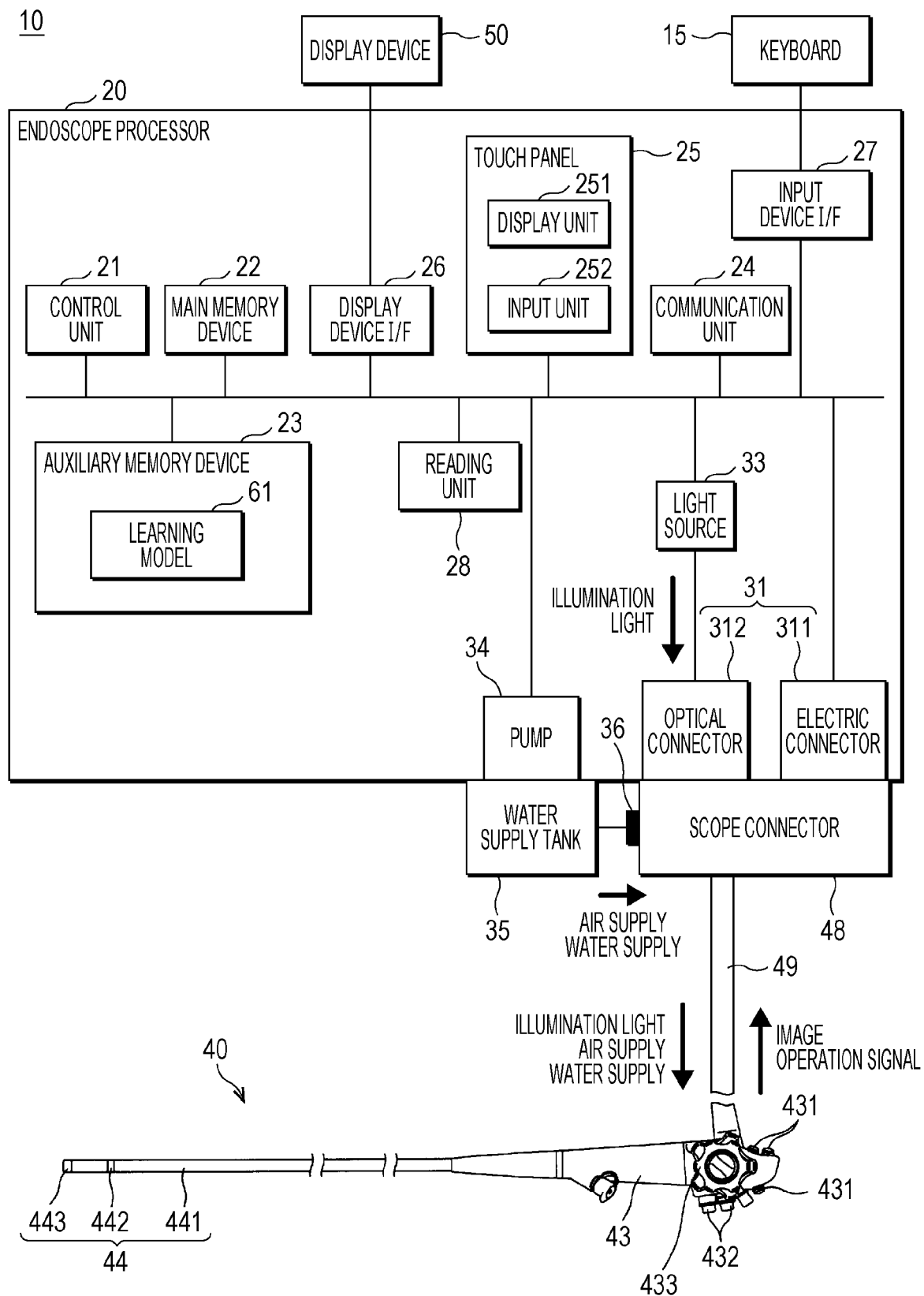
FIG. 4 is an explanatory diagram for explaining the configuration of the endoscope system.

FIG. 4 is an explanatory diagram for explaining the configuration of the endoscope system 10. As described above, the endoscope system 10 includes the endoscope processor 20, the endoscope 40, and the display device 50. In addition to the touch panel 25 and the reading portion 28, the endoscope processor 20 includes a control unit 21, a main memory device 22, an auxiliary memory device 23, a communication unit 24, a display device I/F (Interface) 26, and an input device I/F 27, an endoscope connector 31, a light source 33, a pump 34, and a bus. The endoscope connector 31 includes an electric connector 311 and an optical connector 312.

The control unit 21 is an arithmetic control device that executes a program of this embodiment. One or a plurality of CPUs (Central Processing Units), a multi-core CPU, or the like is used for the control unit 21. The control unit 21 is connected to each hardware unit constituting the endoscope processor 20 via the bus.

The main memory device 22 is a memory device such as an SRAM (Static Random Access Memory), a DRAM (Dynamic Random Access Memory), and a flash memory. The main memory device 22 temporarily holds information necessary during the processing performed by the control unit 21 and a program being executed by the control unit 21.

The auxiliary memory device 23 is a memory device such as an SRAM, a flash memory, or a hard disk. The auxiliary memory device 23 holds the learning model 61, a program to be executed by the control unit 21, and various data necessary for executing the program. The learning model 61 may be stored in an external large-capacity memory device connected to the endoscope processor 20.

The communication unit 24 is an interface for data communication between the endoscope processor 20 and the network. The touch panel 25 includes a display unit 251 such as a liquid crystal display panel, and an input unit 252 layered on the display unit 251.

The display device I/F 26 is an interface for connecting the endoscope processor 20 and the display device 50. The input device I/F 27 is an interface for connecting the endoscope processor 20 and an input device such as the keyboard 15.

The light source 33 is a high-intensity white light source such as a xenon lamp. The light source 33 is connected to the bus via a driver (not illustrated). The on/off of the light source 33 and the change of brightness are controlled by the control unit 21. The illumination light emitted from the light source 33 is incident on the optical connector 312. The optical connector 312 engages with the scope connector 48 to supply illumination light to the endoscope 40.

The pump 34 generates pressure for the air supply/water supply function of the endoscope 40. The pump 34 is connected to the bus via a driver (not illustrated). The on/off and pressure change of the pump 34 are controlled by the control unit 21. The pump 34 is connected to the air/water supply port 36 provided in the scope connector 48 via a water supply tank 35.

The function of the endoscope 40 connected to the endoscope processor 20 will be outlined. A fiber bundle, a cable bundle, an air supply tube, a water supply tube, and the like are inserted inside the scope connector 48, the universal cord 49, the operation unit 43, and the insertion portion 44. The illumination light emitted from the light source 33 is radiated from an illumination window provided at the distal tip 443 via the optical connector 312 and the fiber bundle.

The range illuminated by the illumination light is captured by an image sensor provided at the distal tip 443. The captured image is transmitted from the image sensor to the endoscope processor 20 via the cable bundle and the electric connector 311.

The control unit 21 performs image processing on the captured image to generate the endoscope image 59 that makes it easy for the user to visually find a lesion. As described with reference to FIG. 1, the control unit 21 performs image processing on the original image 56 to generate a plurality of processed images 57. The control unit 21 acquires the disease status output from the learning model 61.

The control unit 21 extracts the first interest region 581 from the processed image 57 input to the learning model 61, which strongly affects the output from the learning model 61, and generates the interest region image 58. The control unit 21 outputs the endoscope image 59, the disease status, and the interest region image 58 to the display device 50.

Figure 5:
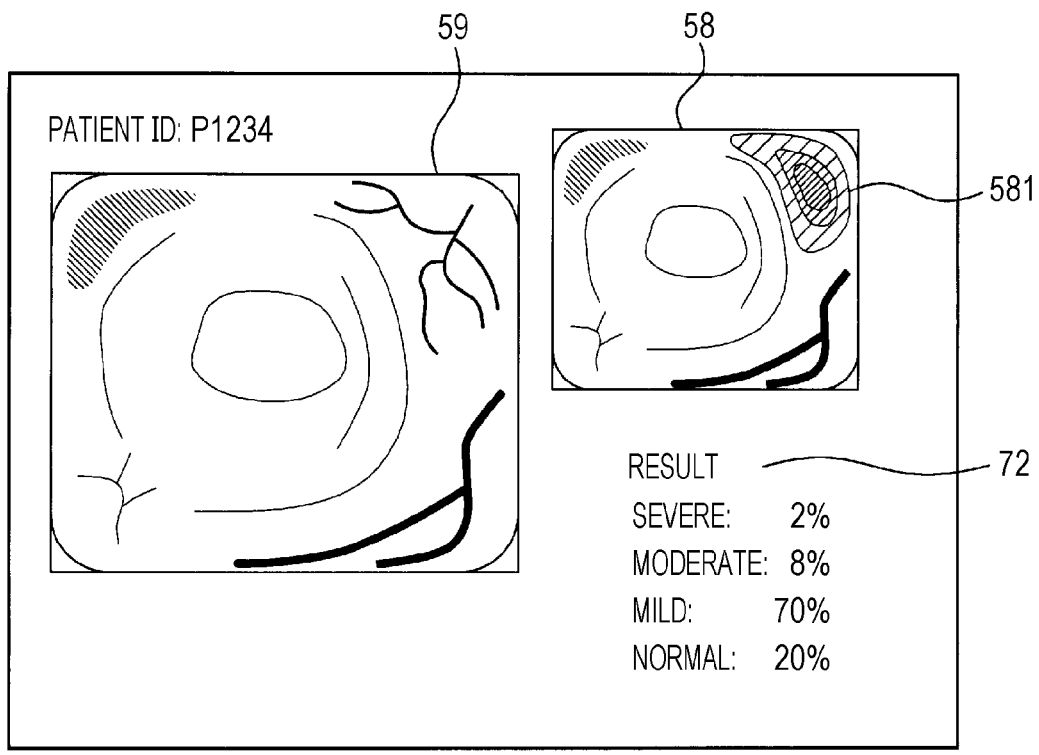
FIG. 5 is an explanatory diagram illustrating an example of a screen displayed on a display device.

FIG. 5 is an explanatory diagram illustrating an example of a screen displayed on the display device 50. On the screen illustrated in FIG. 5, the endoscope image 59, the interest region image 58, and a result field 72 are displayed. In the result field 72, the disease status output from the learning model 61 are listed.

During the endoscopic examination, the endoscope image 59 is updated in real time. The user who operates the endoscope 40 operates the endoscope 40 while observing the endoscope image 59. It is desirable that the interest region image 58 and the result field 72 are also updated in real time, but when the load of the control unit 21 is high, these may be updated at a frame rate which is smaller than the endoscope image 59.

The user observes the endoscope image 59 while referring to the result field 72 and the interest region image 58. As described above, it is possible to prevent oversight of lesions.

For example, when it is determined from the learning model 61 that the probability of having an ulcer is high, the first interest region 581 is a place where an ulcer is likely to occur. If it is determined from the learning model 61 that there is a high probability of having no ulcer, the first interest region 581 is a place which is likely to be a normal mucosa. The user infers the reason for the determination by the learning model 61 based on the information of both the determination result of the disease status and the first interest region 581, and observes the endoscope image 59 as necessary, and make appropriate diagnosis and treatment.

Figure 6:
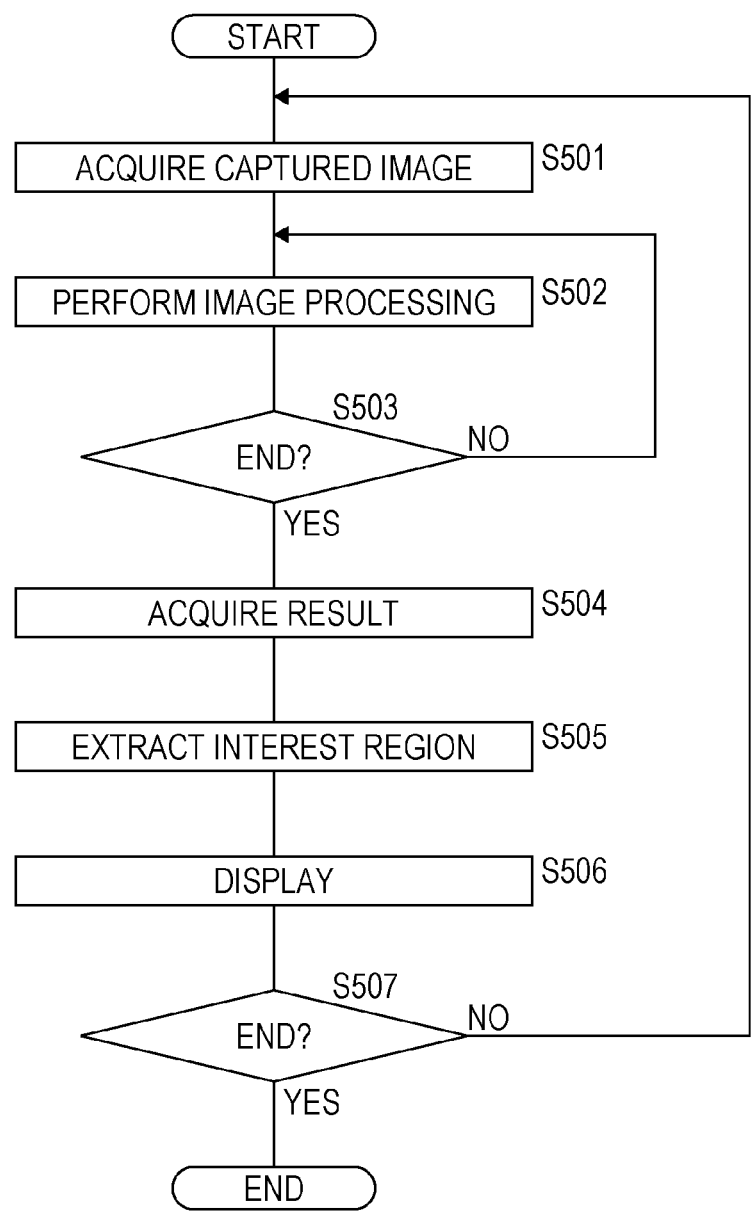
FIG. 6 is a flowchart for explaining a processing flow of a program.

FIG. 6 is a flowchart for explaining the processing flow of a program. The flowchart illustrated in FIG. 6 is executed by the control unit 21. The control unit 21 executes the program illustrated in FIG. 6 together with processing such as generation of the endoscope image 59 and control of the light source 33 and the image sensor arranged at the distal tip 443 of the endoscope 40.

The control unit 21 acquires a captured image from the endoscope 40 (Step S501). The control unit 21 performs image processing and generates the processed image 57 (Step S502). The control unit 21 temporarily stores the generated processed image 57 in the auxiliary memory device 23. The control unit 21 determines whether the generation of the processed image 57 to be input to the learning model 61 has ended (Step S503). If it is determined that the process has not ended (NO in Step S503), the control unit 21 returns to Step S502.

When it is determined that the process has ended (YES in Step S503), the control unit 21 inputs the processed image 57 into the learning model 61 and acquires a disease status output from the output layer 533 (Step S504). The control unit 21 extracts the first interest region 581 that strongly affects the output from the output layer 533 by a method such as Grad-CAM (Step S505). The control unit 21 generates the interest region image 58.

The control unit 21 displays the endoscope image 59, the interest region image 58, and the results acquired from the learning model 61 in Step S504 on the display device 50 (Step S506). The control unit 21 determines whether to end the process (Step S507). For example, when the user instructs the end of the endoscopic examination, or when the endoscope 40 is removed from the endoscope processor 20, the control unit 21 determines that the process ends.

If it is determined that the process does not end (NO in Step S507), the control unit 21 returns to Step S501. If it is determined that the process ends (YES in Step S507), the control unit 21 ends the process.

According to this embodiment, it is possible to provide the endoscope processor 20 having a high ability to detect a lesion.

It is possible to provide the endoscope processor 20 that outputs a disease status using information which may be lost in the endoscope image 59 emphasized on ease of user's viewing by directly using the captured image taken by the endoscope 40 or by using an image in the middle of generating the endoscope image 59 from the captured image.

For example, with the use of a model visualization method such as Grad-CAM, it is possible to provide the endoscope processor 20 which displays a position where a lesion is highly likely to present with a relatively small calculation load compared to the object detection method such as R-CNN. Since the calculation load is low, it is possible to provide the endoscope processor 20 that assists the user's determination without impairing the real-time display required for endoscopic examinations.

The learning model 61 may be generated using any classification algorithm such as SVM (Support Vector Machine), decision tree, random forest, XGBoost, and the like. The learning model 61 may be generated using an arbitrary object detection algorithm such as R-CNN, FastRCNN, Faster RCNN, SSD (Single Shot Multibook Detector), or YOLO (You Only Look Once).

Second Embodiment

This embodiment relates to a server 80 or the like that generates the learning model 61. Descriptions regarding common parts with the first embodiment will be omitted.

FIG. 7 is an explanatory diagram for explaining the configuration of the server 80. The server 80 includes a control unit 81, a main memory device 82, an auxiliary memory device 83, a communication unit 84, and a bus. The control unit 81 is an arithmetic control device that executes the program of this embodiment. One or a plurality of CPUs, a multi-core CPU, a GPU (Graphics Processing Unit), or the like is used for the control unit 81. The control unit 81 is connected to each hardware unit constituting the server 80 via the bus.

The main memory device 82 is a memory device such as an SRAM, a DRAM, and a flash memory. The main memory device 82 temporarily holds information necessary during the processing performed by the control unit 81 and a program being executed by the control unit 81.

The auxiliary memory device 83 is a memory device such as an SRAM, a flash memory, a hard disk, or a magnetic tape. The auxiliary memory device 83 stores the program to be executed by the control unit 81, a training data DB 65, a learning model DB 66, the learning model 61 generated by the control unit 81, and various data necessary for executing the program. The training data DB 65, the learning model DB 66, and the learning model 61 may be stored in an external large-capacity memory device or the like connected to the server 80.

The server 80 is a general-purpose personal computer, a tablet, a large-scaled computer, a virtual machine running on the large-scaled computer, a cloud computing system, or a quantum computer. The server 80 may be a plurality of personal computers or the like that perform distributed processing.

FIG. 8 is an explanatory diagram for explaining the record layout of the training data DB 65. The training data DB 65 is a DB that records training data used to generate the learning model 61. The training data DB 65 has an original image field, a part field, a disease field, and an image processing field. The disease field has subfields related to diseases which output the state using the learning model 61, such as an ulcer field, a tumor field, and a bleeding field.

The image processing field has subfields such as a first processed image field, a second processed image field, and a third processed image field. The training data DB 65 has one record for one original image 56.

The original image 56 is recorded in the original image field. In the part field, the part where the original image 56 has been taken is recorded. Each subfield of the disease field records the disease status as determined by a specialist physician.

For example, the top record in FIG. 8 records a doctor's determination that the original image "A0011.bmp" contained severe ulcers and bleeding and no tumors. When the pathological diagnosis of a biopsy sample taken from the position where the original image 56 has been taken is performed, the result of the pathological diagnosis may be recorded in the disease field.

The first processed image 571 is recorded in the first processed image field. The second processed image 572 is recorded in the second processed image field. The third processed image 573 is recorded in the third processed image field. The same applies to the subsequent subfields of the image processing field.

Each training data is created by a specialist who has a particularly high knowledge of diagnosis using endoscope images. It is more desirable that the training data is created by a so-called expert panel group composed of a plurality of specialists.

As will be described later, the control unit 81 generates the learning model 61 using the training data DB 65. For example, when generating the learning model 61 for ulcer determination described using FIG. 2, the control unit 81 creates the training data by extracting the ulcer field, the first processed image field, the second processed image field, and the third processed image field from the training data DB 65.

FIG. 9 is an explanatory diagram for explaining the record layout of the learning model DB 66. The learning model DB 66 is a DB that records the learning model 61 generated by using the training data DB 65.

The learning model DB 66 has a learning model ID field, a part field, a disease field, and an input data field. The learning model DB 66 has one record for one learning model ID.

In the learning model ID field, a learning model ID uniquely assigned to the learning model 61 is recorded. In the part field, the part targeted by the learning model 61 is recorded. In the disease field, a disease targeted by the learning model 61 is recorded. In the input data field, the input data of the learning model 61 is recorded in combination with an image processing type.

When the learning model 61 is delivered to the endoscope processor 20, the record corresponding to the learning model 61 delivered in the learning model DB 66 is also delivered to the endoscope processor 20.

Figure 10:
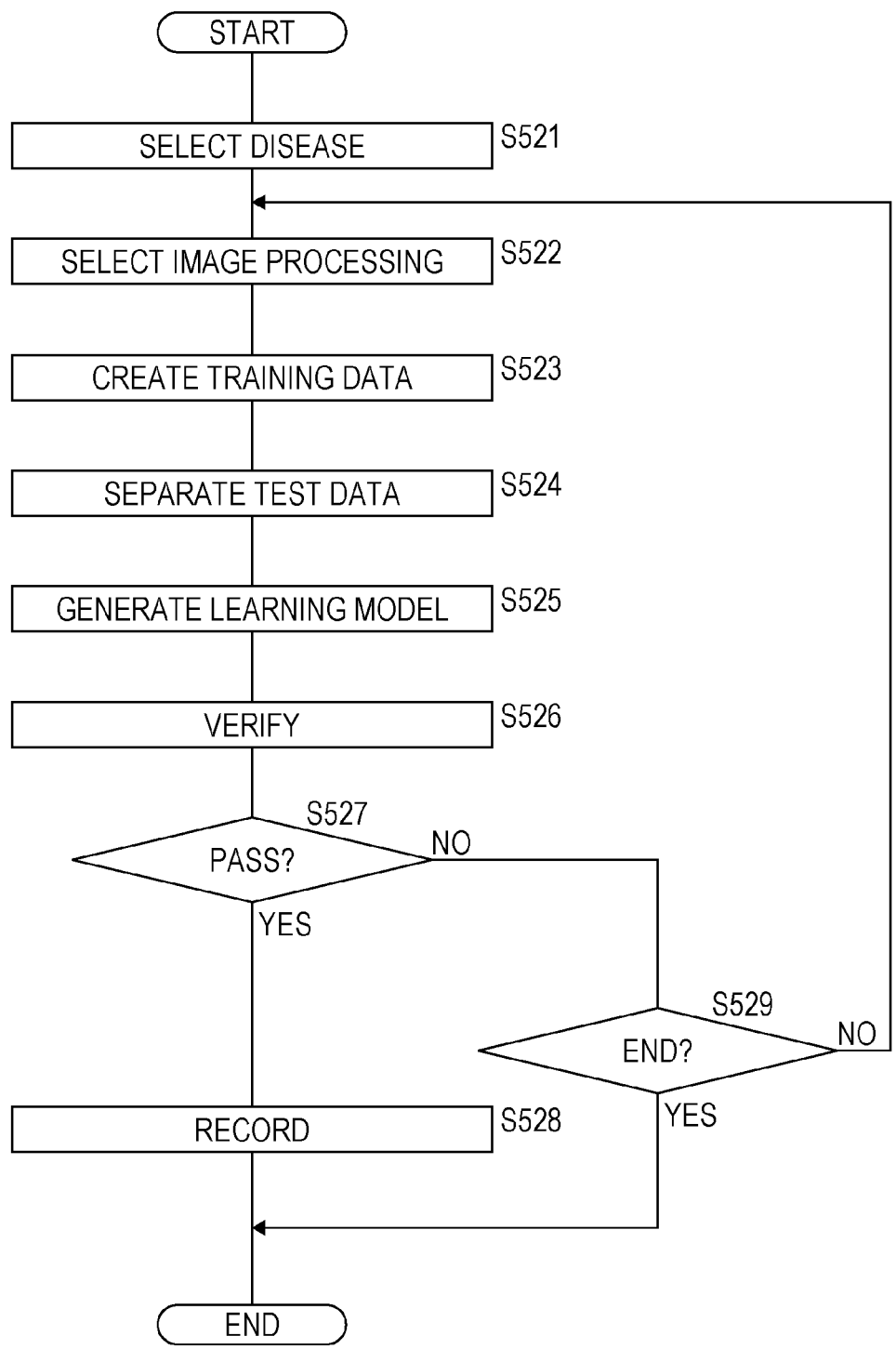
FIG. 10 is a flowchart for explaining a processing flow of a program that generates a learning model.

FIG. 10 is a flowchart for explaining the processing flow of a program that generates the learning model 61. The flowchart illustrated in FIG. 10 is executed by the control unit 81. In FIG. 10, a case where the learning model 61 for a part specified by the user is generated will be described as an example.

The control unit 81 selects the target disease for which the learning model 61 is generated (Step S521). The selection is made, for example, based on an instruction from the user. The control unit 81 selects the image processing to be used (Step S522). The selection is made, for example, based on an instruction from the user. The selection may be made randomly or based on a predetermined rule. The control unit 81 may sequentially select so-called brute force by a permutation combination of available image processing.

The control unit 81 extracts the fields corresponding to the selections of Step S521 and Step S522 from the training data DB 65 and creates training data (Step S523). The control unit 81 separates the extracted training data into teaching data and test data (Step S524). The control unit 81 performs supervised machine learning by calculating the parameters of the intermediate layer 532 using the teaching data and using an error backpropagation method or the like, and generates the learning model 61 (Step S525).

The control unit 81 verifies the accuracy of the learning model 61 using the teaching data (Step S526). The verification is performed by calculating the probability that the output matches the disease field in the teaching data when the processed image 57 in the teaching data is input to the learning model 61.

The control unit 81 determines whether the accuracy of the learning model 61 generated in Step S525 is acceptable (Step S527). If it is determined that the accuracy is acceptable (YES in Step S527), the control unit 81 creates a new record in the learning model DB 66. The control unit 81 records the learning model ID uniquely assigned to the learning model 61, which is created in Step S525, in the learning model ID field.

The control unit 81 records the part targeted by the learning model 61 in the part field, the disease selected in Step S521 in the disease field, and the input data of the generated learning model 61 in the input data field (Step S528). The control unit 81 records the learning model 61 generated in Step S525 in the auxiliary memory device 83 in association with the learning model ID. The control unit 81 ends the process.

If it is determined that the accuracy is not acceptable (NO in Step S527), the control unit 81 determines whether to end the process (Step S529). For example, when the process from Step S522 to Step S529 is repeated a predetermined number of times, the control unit 81 determines that the processing ends. If it is determined that the process does not end (NO in Step S529), the control unit 81 returns to Step S522. If it is determined that the process ends (YES in Step S529), the control unit 81 ends the process.

When a plurality of learning models 61 that are acceptable in Step S527 are generated for the same part and disease, the control unit 81 may delete the record, which contains the learning model 61 having the lower accuracy or the learning model 61 having the larger amount of calculation, from the learning model DB 66.

The learning model 61 generated by the control unit 81 is delivered to the endoscope processor 20 after the procedures such as approval under the Acts on Pharmaceuticals and Medical Devices are completed.

According to this embodiment, the learning model 61 for obtaining a preferable output can be generated. According to this embodiment, one original image 56 can be used to generate the learning models 61 for multiple diseases.

Third Embodiment

This embodiment relates to the endoscope system 10 that outputs a plurality of disease status. Descriptions regarding common parts with the first embodiment will be omitted.

Figure 11:
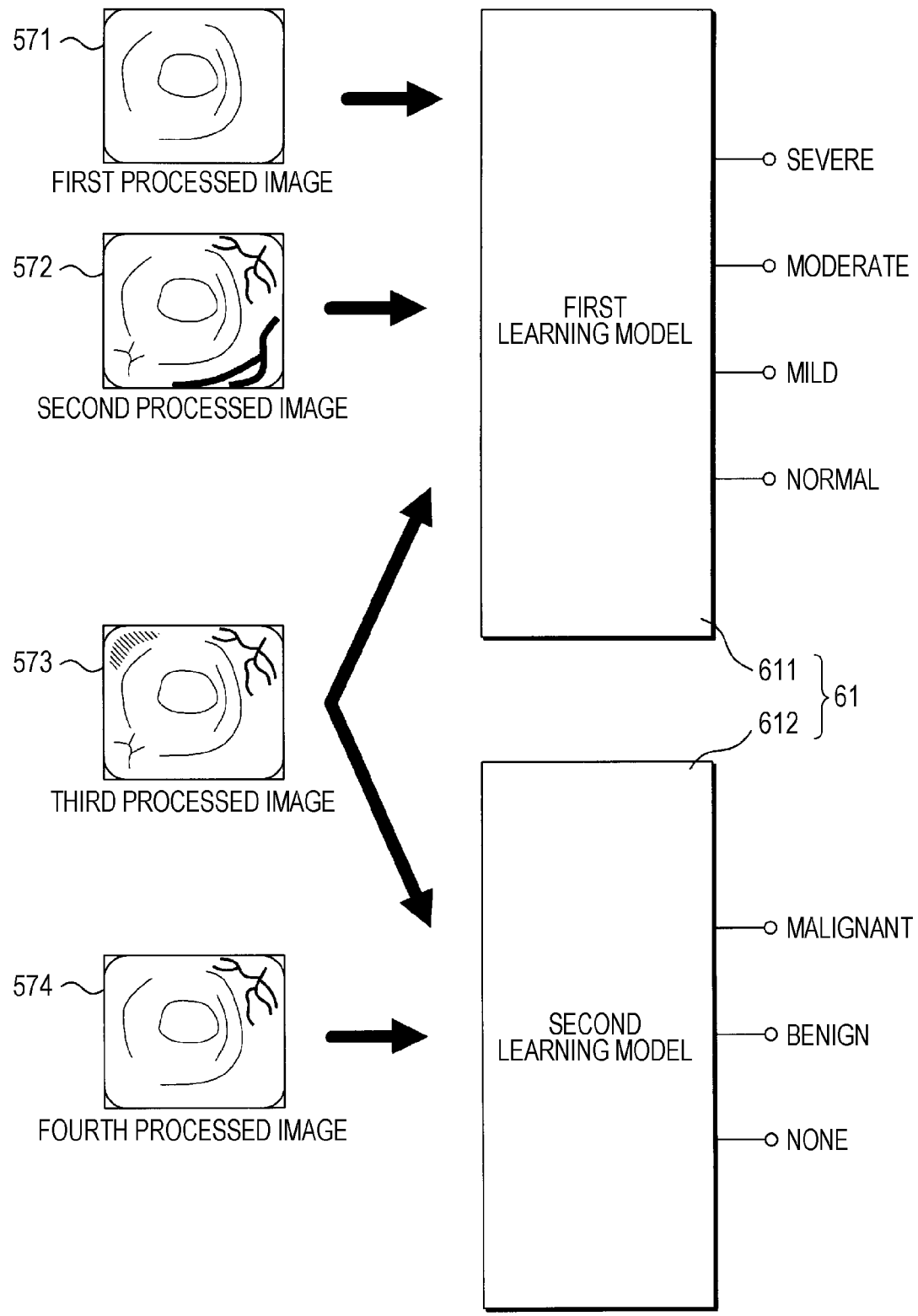
FIG. 11 is an explanatory diagram for explaining the configuration of a learning model of a third embodiment.

FIG. 11 is an explanatory diagram for explaining the configuration of the learning model 61 of the third embodiment. In this embodiment, two learning models 61, a first learning model 611 and a second learning model 612, are used.

Both the first learning model 611 and the second learning model 612 are generated by the control unit 81 as described in the second embodiment, and distributed to the endoscope processor 20 through a predetermined legal procedure. The learning model DB 66 including the record in which the first learning model 611 and the second learning model 612 are recorded is also distributed to the endoscope processor 20.

The first learning model 611 outputs the ulcer status shown in the original image 56 when the three processed images 57 of the first processed image 571, the second processed image 572, and the third processed image 573 are input. The ulcer status output by the first learning model 611 is the probability that the original image 56 contains a severe ulcer, the probability that a moderate ulcer is included, the probability that a mild ulcer is included, and the probability that the ulcer is not included.

The second learning model 612 outputs the tumor status shown in the original image 56 when the two processed images 57 of the third processed image 573 and the fourth processed image 574 are input. The ulcer status output by the second learning model 612 is the probability that the original image 56 includes a malignant tumor, the probability that a benign tumor is included, and the probability that the tumor is not included.

Figure 12:
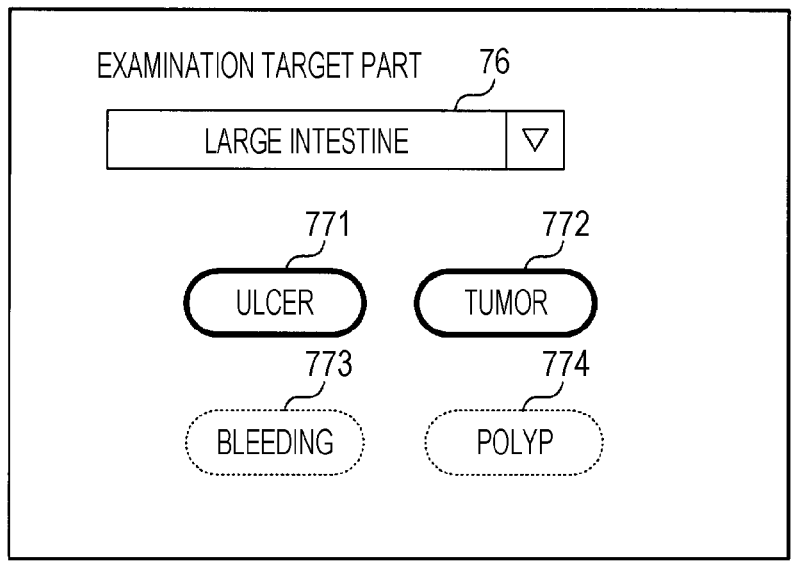
FIG. 12 is an explanatory diagram illustrating an example of a screen displayed on a touch panel.

FIG. 12 is an explanatory diagram illustrating an example of a screen displayed on the touch panel 25. The screen illustrated in FIG. 12 includes an examination target part field 76, an ulcer button 771, a tumor button 772, a bleeding button 773, and a polyp button 774. The examination target part field 76 is a pull-down menu type button. The user can operate the examination target part field 76 to select the target part for endoscopic examination.

The ulcer button 771, the tumor button 772, the bleeding button 773, and the polyp button 774 are toggle buttons that can be turned on or off, respectively. The user can use these buttons to select a disease that uses the learning model 61. FIG. 12 illustrates a state in which the target part is the large intestine and the ulcer button 771 and the tumor button 772 are selected.

Figure 13:
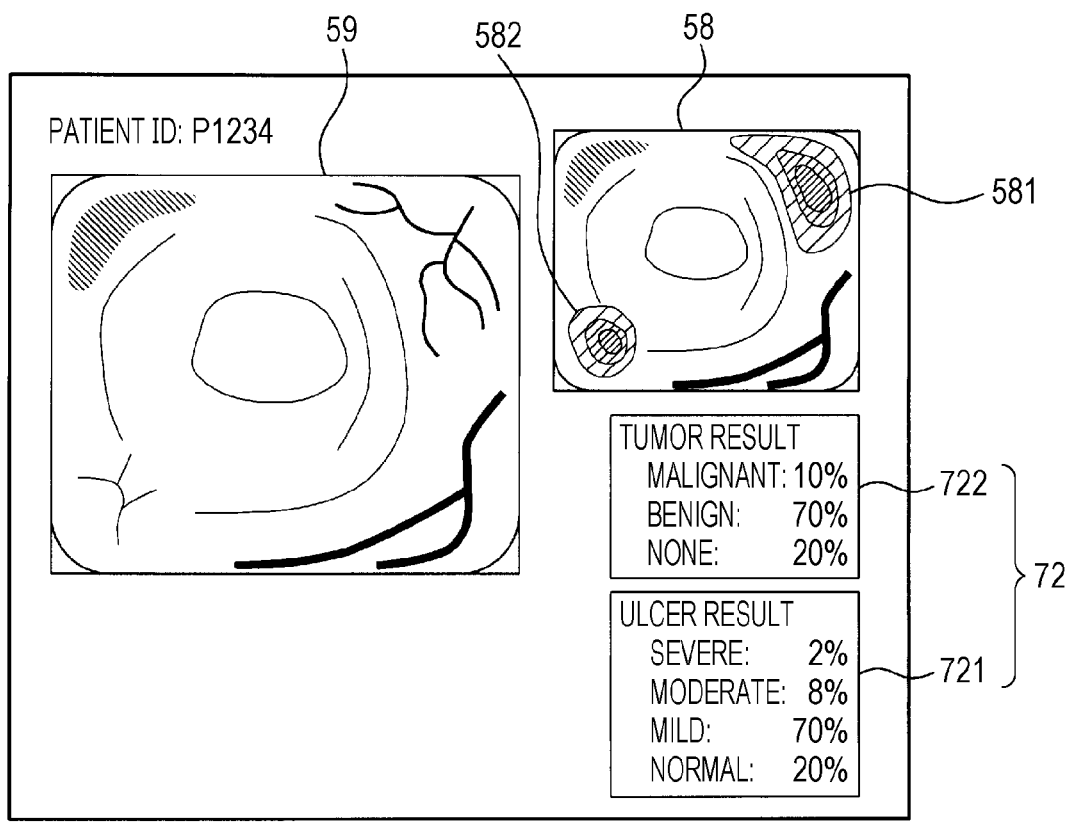
FIG. 13 is an explanatory diagram illustrating an example of a screen displayed on the display device of the third embodiment.

FIG. 13 is an explanatory diagram illustrating an example of a screen displayed on the display device 50 of the third embodiment. On the screen illustrated in FIG. 13, the endoscope image 59, the interest region image 58, and a result field 72 are displayed. The interest region image 58 includes a first interest region 581 and a second interest region 582. The result field 72 includes a first result field 721 and a second result field 722.

In the first result field 721, the ulcer status output from the first learning model 611 is displayed. It is determined that the region shown in the original image 56 has a 2% probability of having a severe ulcer, an 8% probability of having a moderate ulcer, a 70% probability of having a mild ulcer, and a 20% change of no ulcer.

In the second result field 722, the tumor status output from the second learning model 612 is displayed. It has been determined that the region shown in the original image 56 has a 10% probability of having a malignant tumor, a 70% probability of having a benign tumor, and a 20% probability of having no tumor.

The first interest region 581 is a region in the processed image 57 input to the first learning model 611 which strongly affects the output. The second interest region 582 is a region in the processed image 57 input to the second learning model 612 which strongly affects the output.

The control unit 21 performs color-coded display such as displaying the first result field 721 and the first interest region 581 in a reddish color, and the second result field 722 and the second interest region 582 in a bluish color. The color-coded display allows the user to easily distinguish between the part that has affected the determination of the ulcer and the part that has affected the determination of the tumor.

The examination target part field 76, the ulcer button 771, the tumor button 772, the bleeding button 773, the polyp button 774, and the like described using FIG. 12 may be displayed in the margin of the display screen described using FIG. 13. The user can switch the disease for which the determination is made without moving the line of sight from the display device 50.

The control unit 21 may accept operations of the examination target part field 76 and the like displayed on the display device 50 via the keyboard 15 or the like or a mouse or the like. The display device 50 may have a touch panel function. The control unit 21 may accept operations of the examination target part field 76 and the like displayed on the display device 50 by a voice recognition function via a microphone (not illustrated).

Figure 14:
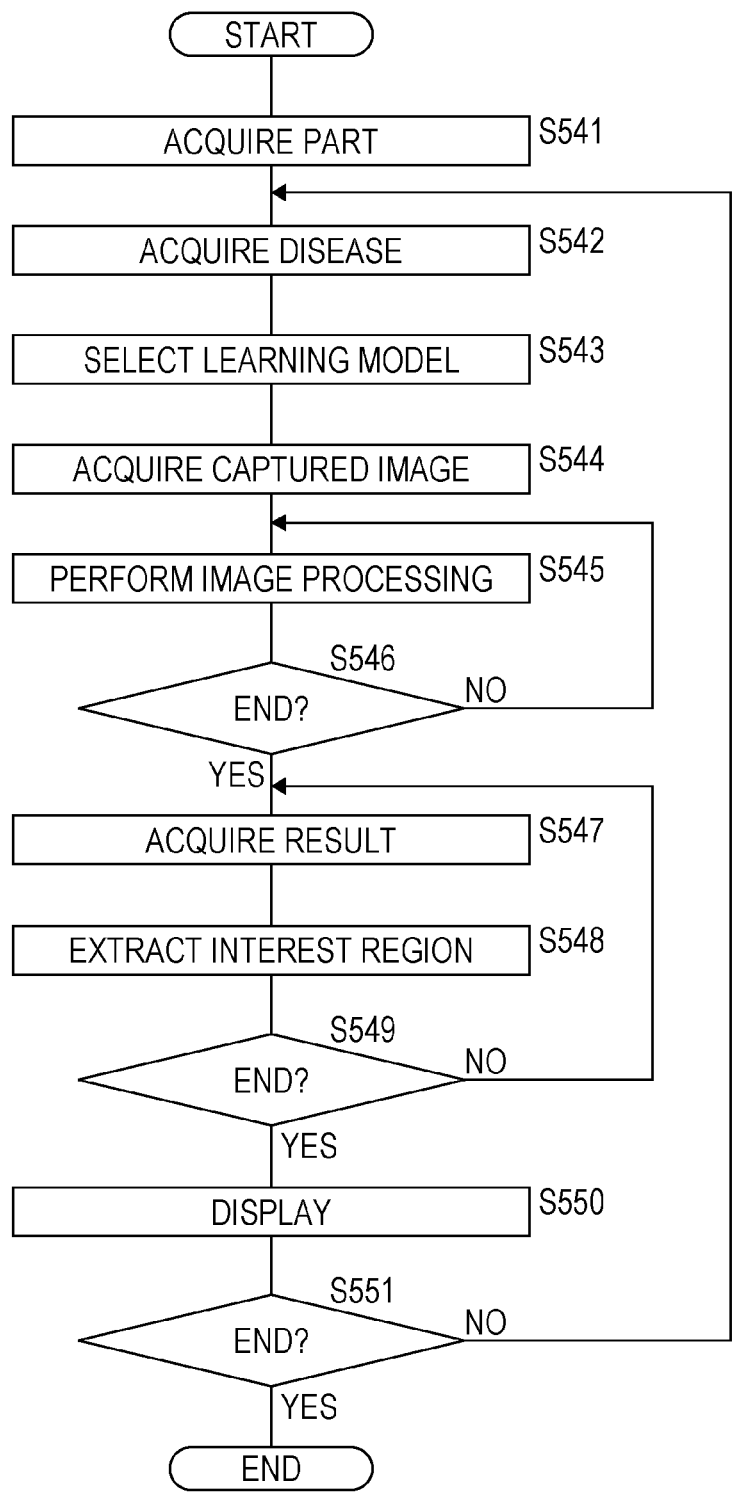
FIG. 14 is a flowchart for explaining a processing flow of a program of the third embodiment.

FIG. 14 is a flowchart for explaining a processing flow of the program of the third embodiment. The flowchart illustrated in FIG. 14 is executed by the control unit 21.

The control unit 21 acquires the target part for endoscopic examination via the examination target part field 76 (Step S541). The control unit 21 acquires a disease using the learning model 61 via the ulcer button 771, the tumor button 772, the bleeding button 773, the polyp button 774, and the like (Step S542).

The control unit 21 searches the learning model DB 66 using the part acquired in Step S541 and the disease acquired in Step S542 as keys, and extracts a record. The control unit 21 selects the learning model 61 to be used in the subsequent process based on the learning model ID recorded in the learning model ID field of the extracted record (Step S543). When a plurality of diseases are selected by the user, a plurality of learning models 61 are selected in Step S543.

The control unit 21 acquires a captured image from the endoscope 40 (Step S544). The control unit 21 performs image processing and generates the processed image 57 (Step S545). The control unit 21 temporarily stores the generated processed image 57 in the auxiliary memory device 23.

The control unit 21 determines whether the generation of the processed image 57 to be input to all the learning models 61 selected in Step S543 has ended (Step S546). If it is determined that the process has not ended (NO in Step S546), the control unit 21 returns to Step S545.

When it is determined that the process has ended (YES in Step S546), the control unit 21 inputs the processed image 57 into one of the learning models 61 selected in Step S543 to acquire the disease status output from the output layer 533 (Step S547). The control unit 21 extracts a region of interest that strongly affects the output from the output layer 533 by a method such as Grad-CAM (Step S548). The control unit 21 temporarily stores the disease status and the region of interest in the auxiliary memory device 23.

The control unit 21 determines whether the processes of all the learning models 61 selected in Step S543 have ended (Step S549). If it is determined that the process has not ended (NO in Step S549), the control unit 21 returns to Step S547.

When it is determined that the process has ended (YES in Step S549), the control unit 21 combines the interest region extracted in Step S548 to generate the interest region image 58. The control unit 21 displays the endoscope image 59, the interest region image 58, and the results acquired from the learning model 61 in Step S547 on the display device 50 (Step S550).

The control unit 21 determines whether to end the process (Step S551). If it is determined that the process does not end (NO in Step S551), the control unit 21 returns to Step S542. If it is determined that the process ends (YES in Step S551), the control unit 21 ends the process.

According to this embodiment, it is possible to provide the endoscope system 10 that displays a plurality of disease statuses. If it is determined that the process has not end in Step S551, the control unit 21 returns to Step S542, so that the control unit 21 accepts a change in the target disease using the learning model 61 during the endoscopic examination. Therefore, the user can refer to the determination by the learning model 61 at any time for the disease of concern in the field of view during the observation using the endoscope image 59.

The control unit 21 may output the disease status using a different learning model 61 for each frame of the endoscope image 59. For example, in the even frame, the control unit 21 uses the first learning model 611 to output the disease status, and in the odd frame, the control unit 21 uses the second learning model 612 to output the disease status. That is, in the screen described with reference to FIG. 13, the first result field 721 is updated in odd frames, and the second result field 722 is updated in even frames. The load on the control unit 21 can be reduced.

Fourth Embodiment

This embodiment relates to the endoscope system 10 capable of selecting the processed image 57 to be used. Descriptions regarding common parts with the first embodiment will be omitted.

FIG. 15 is an explanatory diagram for explaining a record layout of the learning model DB 66 of the fourth embodiment. The learning model DB 66 has a learning model ID field, a part field, a disease field, and an input data field. The input data field has subfields such as a first processed image field, a second processed image field, and a third processed image field. The learning model DB 66 has one record for one learning model ID.

In the learning model ID field, a learning model ID uniquely assigned to the learning model 61 is recorded. In the part field, the part targeted by the learning model 61 is recorded. In the disease field, a disease targeted by the learning model 61 is recorded.

In the first processed image field, whether the first processed image 571 is input to the learning model 61 is recorded. A "1" in the first processed image field indicates that the first processed image 571 is input to the learning model 61. A "0" in the first processed image field indicates that the first processed image 571 is not input to the learning model 61. The same applies to the second and subsequent processed image fields.

Figure 16:
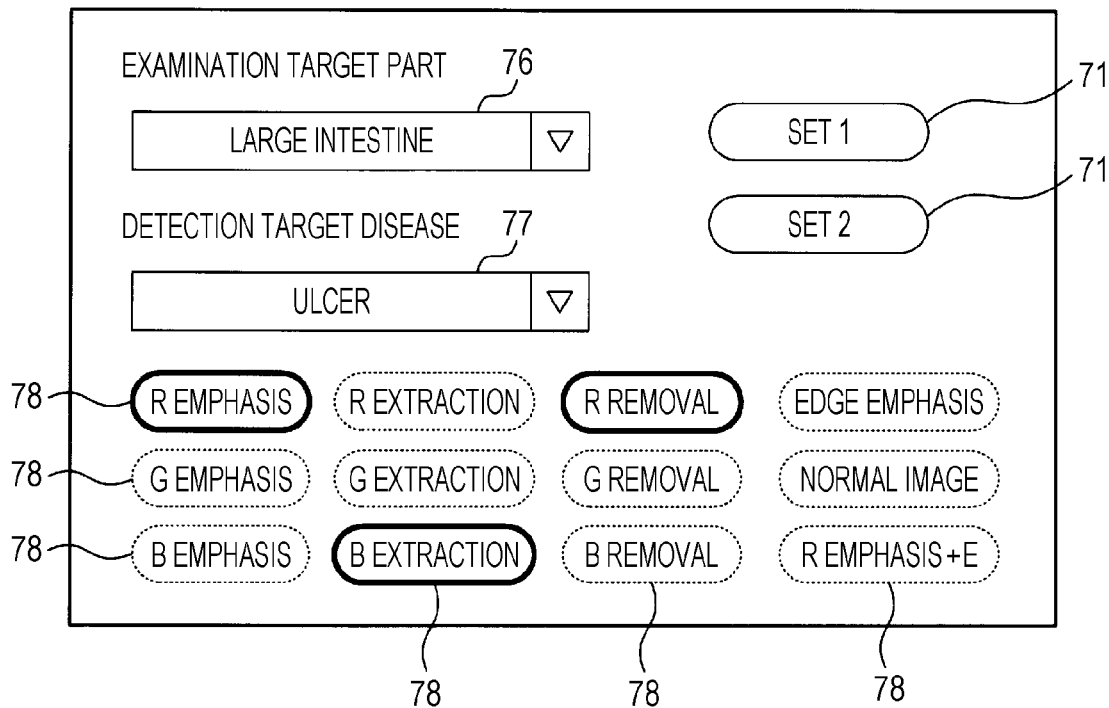
FIG. 16 is an explanatory diagram illustrating an example of a screen displayed on a touch panel of the fourth embodiment.

FIG. 16 is an explanatory diagram illustrating an example of a screen displayed on the touch panel 25 of the fourth embodiment. The screen illustrated in FIG. 16 includes an examination target part field 76, a detection target disease field 77, twelve image processing selection buttons 78, and two set selection buttons 71. The examination target part field 76 and the detection target disease field 77 are pull-down menu type buttons. The image processing selection button 78 and the set selection button 71 are toggle buttons that can be set to the on state or the off state, respectively.

The user can operate the examination target part field 76 to select the target part for endoscopic examination. The user can operate the detection target disease field 77 to select a disease for which the learning model 61 is used. The user uses the image processing selection button 78 to select the image processing method used to generate the processed image 57.

For example, when the image processing selection button 78 of "R emphasis" is on, the processed image 57 that has been subjected to image processing that emphasizes the R component of each pixel of the original image 56 is input to the learning model 61. FIG. 16 illustrates a state in which the image processing selection buttons 78 of "R emphasis", "R removal", and "B extraction" are selected.

The control unit 21 searches the learning model DB 66 using the selected states of the examination target part field 76, the detection target disease field 77, and the respective image processing selection button 78 as keys, and extracts a record. The control unit 21 uses the learning model 61 corresponding to the learning model ID recorded in the learning model ID field of the extracted record to display the result field 72 and the interest region image 58 in FIG. 17 described later.

A recommended combination of image processing is set in the set selection button 71. The combination of image processing set in each set selection button 71 is stored in the auxiliary memory device 23.

When the user turns on the set selection button 71, the state of the image processing selection button 78 is changed to the state set in the set selection button 71. The control unit 21 determines the learning model 61 to be used based on the learning model DB 66, as in the case where the user directly selects the image processing selection button 78.

The user may be able to set a combination of image processing corresponding to each set selection button 71. The set selection button 71 may be set with a combination of image processing suitable for determining various diseases. In doing so, the set selection button 71 may display the name of a suitable disease, such as "for ulcers" or "for tumors".

Figure 17:
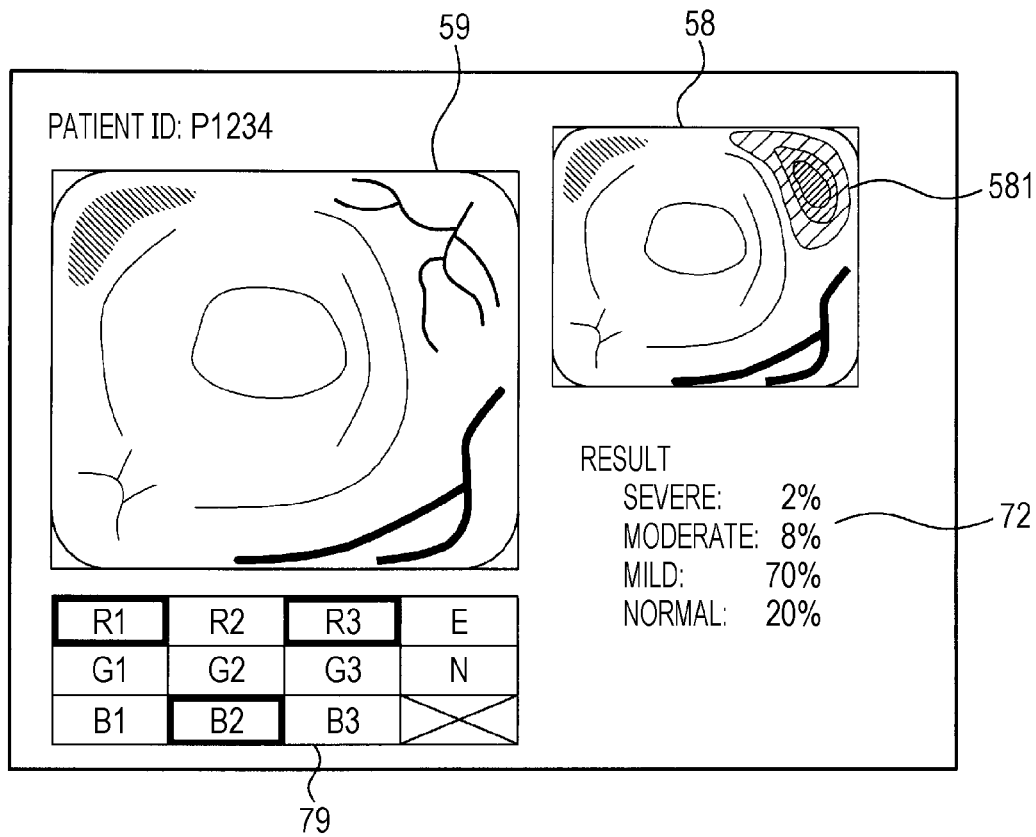
FIG. 17 is an explanatory diagram illustrating an example of a screen displayed on the display device of the fourth embodiment.

FIG. 17 is an explanatory diagram illustrating an example of a screen displayed on the display device 50 of the fourth embodiment. On the screen illustrated in FIG. 17, the endoscope image 59, the interest region image 58, the result field 72, and an image processing selection field 79 are displayed.

In the result field 72, the disease status output from the learning model 61 are listed. In the image processing selection field 79, the presence/absence of selection of the image processing selection button 78 described with reference to FIG. 16 is displayed in a list. For example, "R1" in the image processing selection field 79 corresponds to the image processing selection button 78 of "R emphasis", and "R2" in the image processing selection field 79 corresponds to the image processing selection button 78 of "R extraction". When the image processing selection button 78 of "R emphasis" is on, the "R1" part of the image processing selection field 79 is highlighted.

The image processing selection field 79 may also serve as an image processing selection button 78 that accepts a user's selection. In this case, the control unit 21 receives the operation of the image processing selection field 79 displayed on the display device 50 via the keyboard 15 or the like or the mouse or the like.

The processing flow of the program of the fourth embodiment is the same as the processing flow of the program of the third embodiment described with reference to FIG. 14. However, in this embodiment, the learning model DB 66 described with reference to FIG. 15 in Step S543 is used. That is, the control unit 21 searches the learning model DB 66 using the part acquired in Step S541, the disease acquired in Step S542, and the presence/absence of each processed image 57 by the image processing selection button 78 as keys, and extracts a record.

If the learning model 61 corresponding to the combination of the processed images 57 selected by the user has not been generated, the control unit 21 displays that fact on the touch panel 25 or the display device 50 to encourage the user to reselect. The control unit 21 may present the user with the learning model 61 that uses a combination of processed images 57 similar to the user's selection as an alternative.

Fifth Embodiment

This embodiment relates to a server 80 or the like that updates the learning model 61. Descriptions regarding common parts with the second embodiment will be omitted.

FIG. 18 is an explanatory diagram for explaining a record layout of the additional training data DB according to the fifth embodiment. The additional training data DB is a DB that records additional training data used for updating the learning model 61. The additional training data DB has an original image field, a part field, a disease field, an input data field, and a determination result field. The input data field has subfields such as a first processed image field, a second processed image field, and a third processed image field.

The original image 56 is recorded in the original image field. In the part field, the part where the original image 56 has been taken is recorded. In the disease field, the type of disease determined by a specialist doctor is recorded.

In the first processed image field, it is recorded whether the first processed image 571 has been input to the learning model 61 when the training data is created. "1" in the first processed image field indicates that the first processed image 571 has been input to the learning model 61. "0" in the first processed image field indicates that the first processed image 571 has not been input to the learning model 61. The same applies to the second and subsequent processed image fields. In the determination result field, the disease status determined by a specialist doctor is recorded. The additional training data DB has one record for a set of training data.

Each additional training data is created by a specialist who has a particularly high knowledge of diagnosis using endoscope images. It is more desirable that the additional training data is created by a so-called expert panel group composed of a plurality of specialists.

A specific example of additional training data will be described. The top record of FIG. 18 records additional training data in which an expert and others have determined the ulcer status using the original image of "B0111.bmp", which is a photograph of the "stomach". The expert has referred to the learning model 61, which used the first processed image 571, the fourth processed image 574, and the like as inputs. The expert has determined that the ulcer is "severe".

In the second record from the top of FIG. 18, the additional training data in which the expert and others have determined the tumor status is recorded using the same original image of "B0111.bmp". The expert has referred to the learning model 61, which uses the third processed image 573 and the like as inputs. The expert has determined that the tumor is "none".

Figure 19:
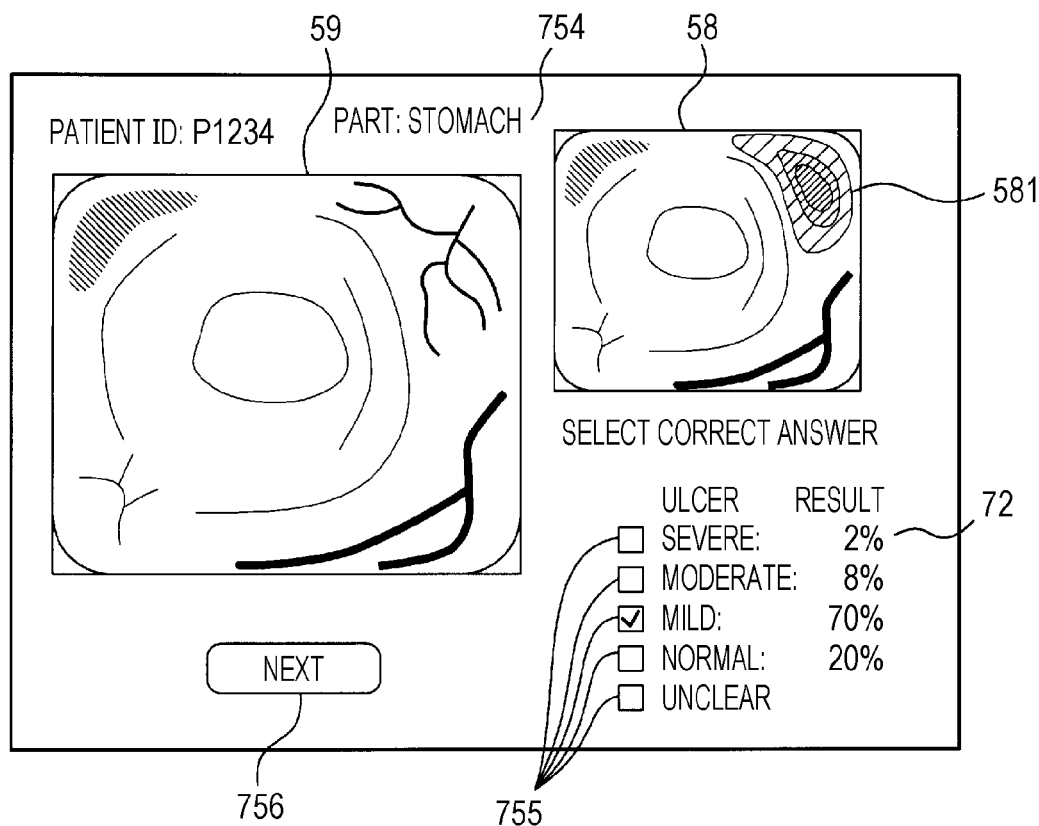
FIG. 19 is an explanatory diagram illustrating an example of a screen for adding training data.

FIG. 19 is an explanatory diagram illustrating an example of a screen for adding training data. On the screen illustrated in FIG. 19, the endoscope image 59, the interest region image 58, the result field 72, a part field 754, and a next button 756 are displayed. A correct answer input field 755 is displayed at the left end of the result field 72. As illustrated in the upper part of the result field 72, in FIG. 19, the result of using the learning model 61 for the ulcer is displayed in the result field 72.

In this embodiment, a case where the learning model 61 is selected in the same manner as in the fourth embodiment will be described as an example. A specialist or the like uses a user interface screen similar to the screen of the touch panel 25 described with reference to FIG. 19 to select the image processing to be used. The learning model 61 is selected based on the combination of the part, the disease, and the image processing selected by the user.

The specialist or the like determines the ulcer status by looking at the endoscope image 59, and selects one of the correct answer input fields 755. If the endoscope image 59 is not suitable for determining the ulcer status, the specialist or the like selects "Unknown" provided at the bottom of the result field 72.

In FIG. 19, "mild" is selected. When the accuracy of the learning model 61 is sufficiently high, the burden on the specialist or the like can be reduced by setting the correct answer input field 755 corresponding to the item with the highest probability to be selected by default.

The specialist or the like can refer to a patient's medical record or the like by selecting, for example, the patient ID displayed on the upper left of the screen. The specialist or the like can accurately determine the disease status by referring to the patient's medical records and the like. After the specialist's determination is entered, an additional record is recorded in the additional training data DB.

When the next button 756 is selected by the specialist or the like, a screen for setting the learning model 61 to be used next is displayed. After that, the interest region image 58 and the result field 72 are updated with the result of using the set learning model 61.

Figure 20:
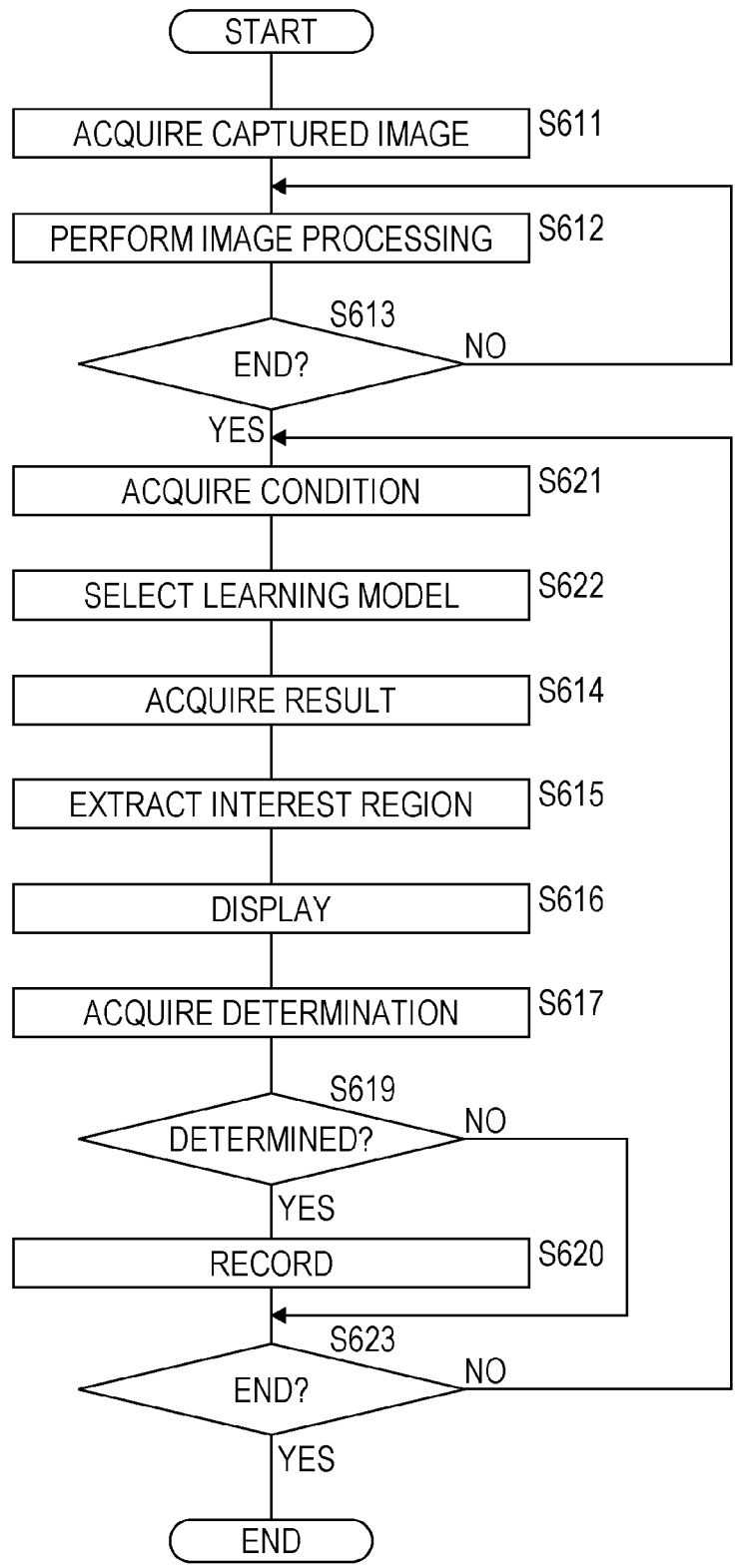
FIG. 20 is a flowchart for explaining a processing flow of a program for acquiring additional training data.

FIG. 20 is a flowchart for explaining a processing flow of a program for acquiring additional training data. The program illustrated in FIG. 20 is executed by a client connected to a server via a network. A case where the client is a so-called thin client that provides only a user interface, and the program is executed by the control unit 81 will be described as an example. The configuration of the client is omitted.

The program illustrated in FIG. 20 may be executed by the control unit of the client. The program illustrated in FIG. 20 may be executed by the control unit 21 of the endoscope processor 20.

The control unit 81 acquires a captured image taken and saved at a hospital and the like in various places (Step S611). The control unit 81 performs image processing and generates the processed image 57 (Step S612). The control unit 81 temporarily stores the generated processed image 57 in the auxiliary memory device 23.

The control unit 81 determines whether the generation of the processed image 57 to be input to the learning model 61 has ended (Step S613). If it is determined that the process has not ended (NO in Step S613), the control unit 81 returns to Step S612.

When it is determined that the process has ended (YES in Step S613), the control unit 81 displays a user interface screen similar to the screen of the touch panel 25 described with reference to FIG. 19, and sets the learning model 61 to be used, that is, acquires a combination of the part, the disease, and the image processing (Step S621).

The control unit 81 searches the learning model DB 66 described with reference to FIG. 15 using the condition acquired in Step S621 as a key, and extract a record. The control unit 81 selects the learning model 61 to be used in the subsequent process based on the learning model ID recorded in the learning model ID field of the extracted record (Step S622).

If the learning model 61 corresponding to the combination of the processed images 57 selected by the user has not been generated in Step S621, the control unit 81 displays that fact to encourage the user to reselect. The control unit 81 may present the user with the learning model 61 that uses a combination of processed images 57 similar to the user's selection as an alternative.

The control unit 81 inputs the processed image 57 corresponding to the combination of the image processing acquired in Step S621 into the learning model 61 acquired in Step S622, and acquires the disease status output from the output layer 533 (Step S614). The control unit 81 extracts the first interest region 581 (Step S615). The control unit 81 generates the interest region image 58.

The control unit 81 displays the screen described with reference to FIG. 19 on the display unit of the client (Step S616). The endoscope image 59 is stored in association with, for example, a captured image, and is acquired together with the captured image in Step S611. The control unit 81 may perform predetermined image processing on the captured image to generate the endoscope image 59.

The control unit 81 acquires a determination by a specialist or the like via the correct answer input field 755 (Step S617). The control unit 81 determines whether a determination other than "Unknown" has been input in Step S617 (Step S619). When it is determined that a determination other than "Unknown" is input (YES in Step S619), the control unit 81 creates a new record in the additional training data DB and records the data in each field (Step S620).

When it is determined that the determination of "Unknown" has been input (NO in Step S619), or after the end of Step S619, the control unit 81 determines whether to end the process (Step S623). For example, when the user inputs an instruction to end the process, the control unit 81 determines that the process ends.

If it is determined that the process does not end (NO in Step S623), the control unit 81 returns to Step S621. If it is determined that the process ends (YES in Step S623), the control unit 81 ends the process.

Figure 21:
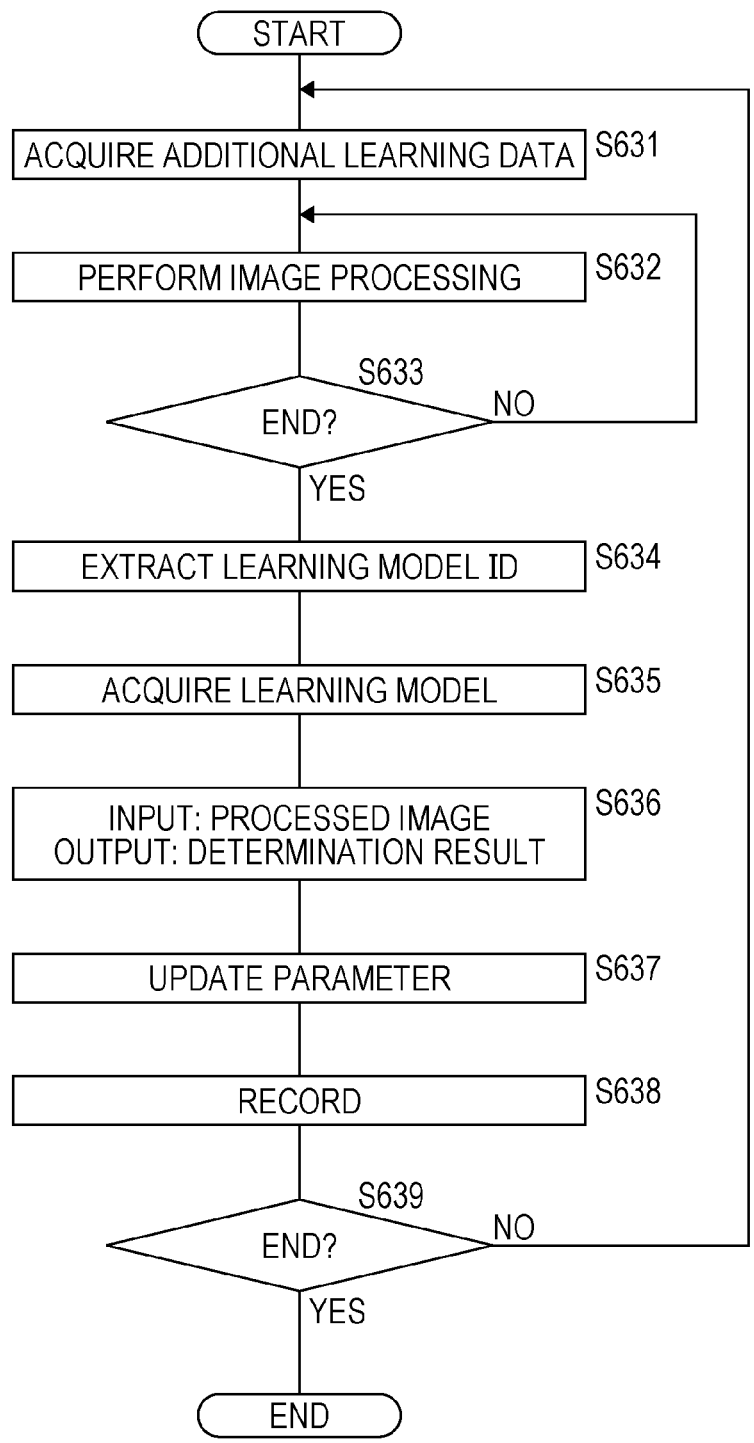
FIG. 21 is a flowchart for explaining a processing flow of a program for updating a learning model.

FIG. 21 is a flowchart for explaining a processing flow of a program for updating the learning model 61. The program described with reference to FIG. 21 is executed when a sufficient number of training data is added to the additional training data DB.

The control unit 81 acquires one record from the additional training data DB (Step S631). The control unit 81 performs image processing corresponding to the input data field in which "1" is recorded for the original image recorded in the original image field, and temporarily stores the original image in the auxiliary memory device 83 (Step S632).

The control unit 81 determines whether the generation of the processed image 57 to be input to the learning model 61 has ended (Step S633). If it is determined that the process has not ended (NO in Step S633), the control unit 81 returns to Step S632.

When it is determined that the process has ends (YES in Step S633), the control unit 81 searches the learning model DB 66 described with reference to FIG. 15 using the part field, the disease field, and the input data field of the additional training data acquired in Step S631 as keys, and extracts a record. The control unit 81 extracts the learning model ID recorded in the learning model ID field of the extracted record (Step S634).

The control unit 81 acquires the learning model 61 corresponding to the extracted learning model ID (Step S635). The control unit 81 sets the processed image 57 stored in Step S632 as the input data of the learning model 61, and sets the determination recorded in the determination result field of the additional training data record as the output of the learning model 61 (Step S636).

The control unit 81 updates the parameter of the learning model 61 by the error backpropagation method (Step S637). The control unit 81 records the updated parameter (Step S638). The control unit 81 determines whether the processing of the record recorded in the additional training data DB has been completed (Step S639). If it is determined that the process has not ended (NO in Step S639), the control unit 81 returns to Step S631. If it is determined that the process has ended (YES in Step S639), the control unit 81 ends the process.

The learning model 61 updated in this embodiment is distributed to the endoscope processor 20 via a network or a recording medium, for example, after the procedure such as approval under the Acts on Pharmaceuticals and Medical Devices. As a result, the learning model 61 is updated.

This embodiment is an example of the method of creating additional training data and updating the learning model 61. The additional training data can be added by any method.

Note that the control unit 81 may update the learning model 61 that uses the processed image 57 different from the combination of the processed images 57 recorded in the input data field of the additional training data DB as the input data. In this case, in Step S634, the control unit 81 extracts the learning model 61 to be updated by using only the part field and the disease field of the additional training data record as keys. The input data field of the additional training data DB is unnecessary.

For example, a specialist or the like may create an additional training data DB based on the endoscope image 59 and the medical information recorded in the medical record without referring to the output of the existing learning model 61. In this case, the input data field is not required in the additional training data DB described with reference to FIG. 18.

When the additional training data DB is created without referring to the output of the existing learning model 61, the control unit 81 takes the combination of the processed images 57 used in the existing learning model 61 as an input, and updates the parameter of the learning model 61.

Sixth Embodiment

This embodiment relates to the endoscope system 10 that predicts and displays an expert's subjective evaluation of the endoscope image 59. Descriptions regarding common parts with the first embodiment will be omitted.

In this embodiment, a score learning model is used in addition to the learning model 61. The score learning model outputs a score that predicts an expert's subjective evaluation when the endoscope image 59 is input.

Figure 22:
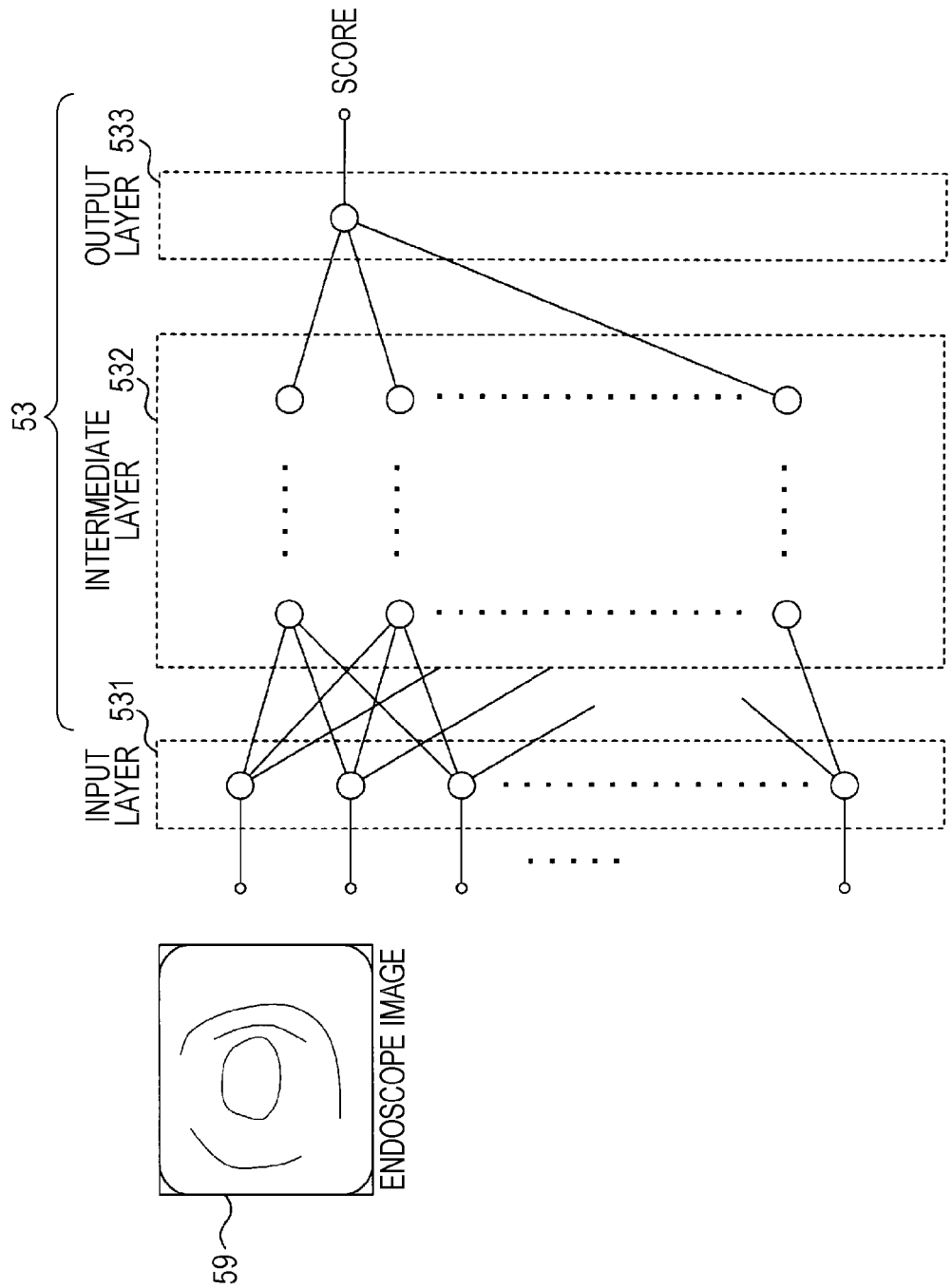
FIG. 22 is an explanatory diagram for explaining the configuration of a score learning model.

FIG. 22 is an explanatory diagram for explaining the configuration of a score learning model. The score learning model is configured by the input layer 531, the intermediate layer 532, the output layer 533, and the neural network model 53 having a convolution layer and a pooling layer (not illustrated).

The endoscope image 59 is input to the score learning model. The input endoscope image 59 is repeatedly processed by the convolution layer and the pooling layer, and then input to the fully-connected layer.

On the output layer 533, a score that predicts the subjective evaluation when the endoscope image 59 is viewed by an expert is output. The parameter of each neuron in the intermediate layer 532 is adjusted by machine learning based on the score training data DB described later.

The score learning model is generated for each part and for each subjective evaluation item to be predicted. Subjective evaluation items are, for example, redness or a vascular see-through level.

Figures 23, 24:
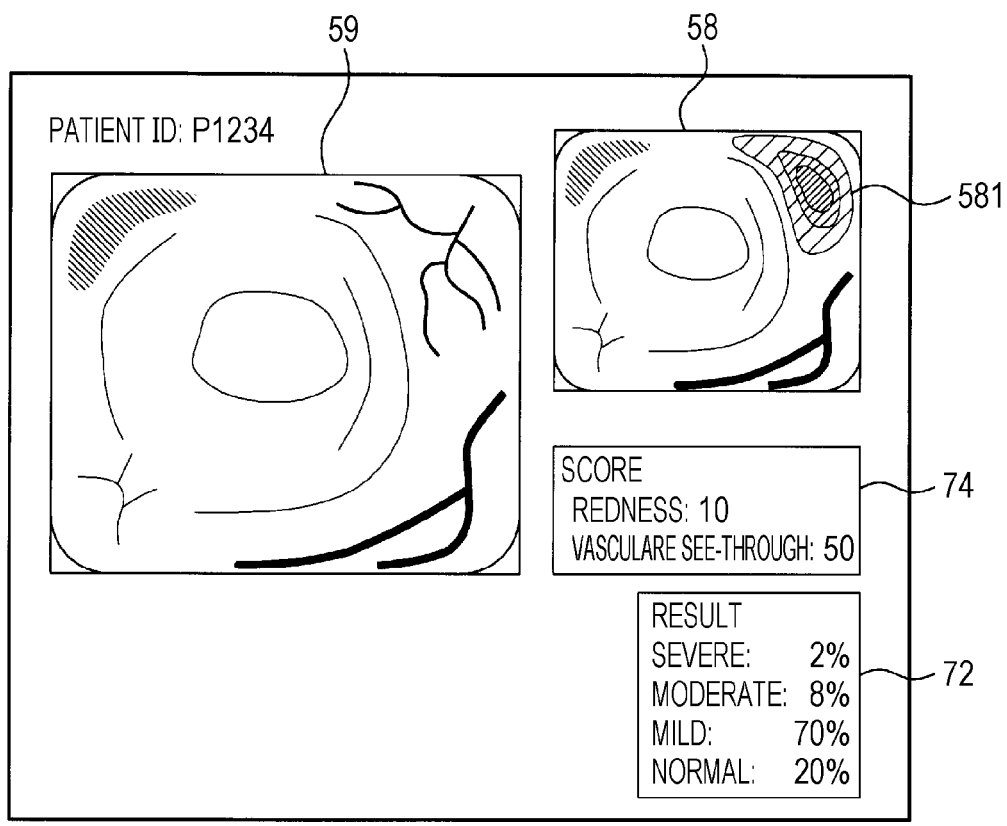
FIG. 23 is an explanatory diagram for explaining a record layout of a score training data DB.
FIG. 24 is an explanatory diagram illustrating an example of a screen displayed on a display device of a sixth embodiment.

FIG. 23 is an explanatory diagram for explaining the record layout of the score training data DB. The score training data DB is a DB that records training data used to generate a score learning model. The score training data DB has an endoscope image field, a part field, and a score field. The score field has subfields for items that are subject to the subjective evaluation of an expert, such as redness fields, vascular see-through fields, and the like.

The endoscope image 59 is recorded in the endoscope image field. In the part field, the part where the endoscope image 59 has been taken is recorded. In the redness field, a score regarding redness determined by a specialist doctor by looking at the endoscope image 59 is recorded. In the vascular see-through field, a score regarding vascular see-through determined by a specialist doctor by looking at the endoscope image 59 is recorded.

For example, the top record in FIG. 23 means that a specialist doctor who has seen the endoscope image "A0051.bmp" has scored 100 points for redness and 10 points for vascular see-through. The score training data DB has one record for one endoscope image 59.

FIG. 24 is an explanatory diagram illustrating an example of a screen displayed on the display device 50 of the sixth embodiment. On the screen illustrated in FIG. 24, the endoscope image 59, the interest region image 58, the result field 72, and a score field 74 are displayed. In the result field 72, the disease status output from the learning model 61 are listed. In the score field 74, the respective scores of redness and vascular see-through output from the score learning model are displayed.

The user refers to the score field 74 to obtain information such as whether a veteran doctor determines that the redness is strong, and uses the information as a reference for diagnosis. From the above, even a relatively inexperienced doctor can make the same diagnosis as a veteran doctor.

Seventh Embodiment

This embodiment relates to the endoscope system 10 realized by operating the endoscope processor 20 and a general-purpose computer 90 in combination. Descriptions regarding common parts with the first embodiment will be omitted.

Figure 25:
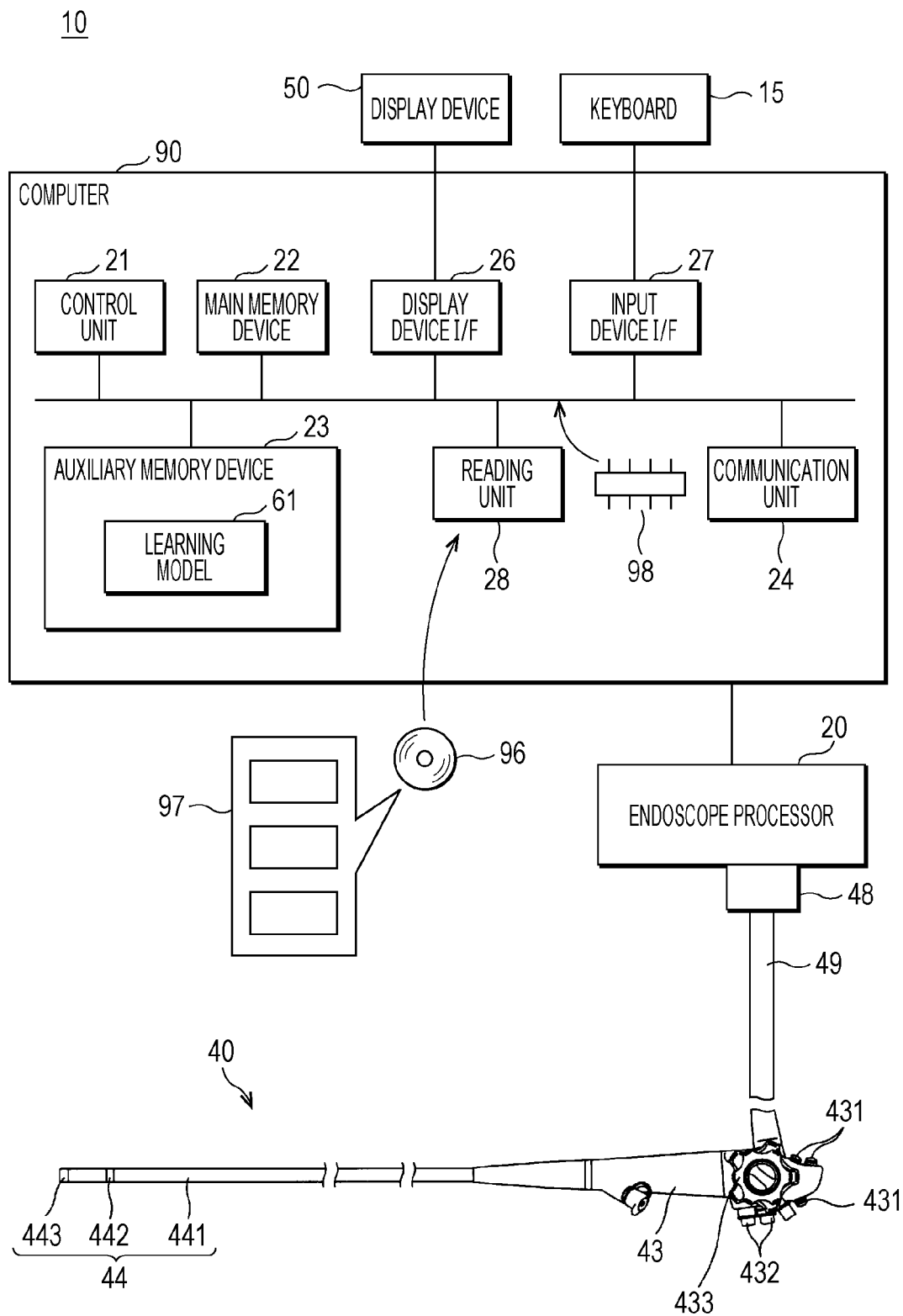
FIG. 25 is an explanatory diagram for explaining the configuration of an endoscope system according to a seventh embodiment.

FIG. 25 is an explanatory diagram for explaining the configuration of the endoscope system 10 according to the seventh embodiment. The endoscope system 10 of this embodiment includes the endoscope processor 20, the endoscope 40, the display device 50, and the computer 90. The endoscope processor 20 generates the endoscope image 59 and controls a built-in light source 33 and the like. The description of the configuration of the endoscope processor 20 will be omitted.

The computer 90 includes the control unit 21, the main memory device 22, the auxiliary memory device 23, the communication unit 24, the display device I/F 26, the input device I/F 27, the reading portion 28, and the bus. The display device 50 is connected to the display device I/F 26. An input device such as the keyboard 15 is connected to the input device I/F 27. The computer 90 is an information device such as a general-purpose personal computer, a tablet, or a server machine.

The computer 90 may be a virtual machine running on a large computer, a cloud computing system, or a quantum computer. The computer 90 may be a plurality of personal computers or the like that perform distributed processing.

The endoscope processor 20 and the computer 90 are connected by a connection cable or wireless communication. The original image 56 and the endoscope image 59 are transmitted from the endoscope processor 20 to the computer 90.

The program 97 described in the first embodiment and the like is recorded on the portable recording medium 96. The control unit 21 reads the program 97 via the reading portion 28 and stores it in the auxiliary memory device 23.

Further, the control unit 21 may read the program 97 stored in a semiconductor memory 98 such as a flash memory mounted in the computer 90. Further, the control unit 21 may download the program 97 from the communication unit 24 and another server computer (not illustrated) connected via a network (not illustrated), and store the program 97 in the auxiliary memory device 23.

The program 97 is installed as a control program for the computer 90 and is loaded and executed in main memory device 22. As described above, the endoscope processor 20 of this embodiment and the computer 90 cooperate with each other to fulfill the functions of the endoscope system 10 described in the first embodiment and the like.

Eighth Embodiment

Figure 26:
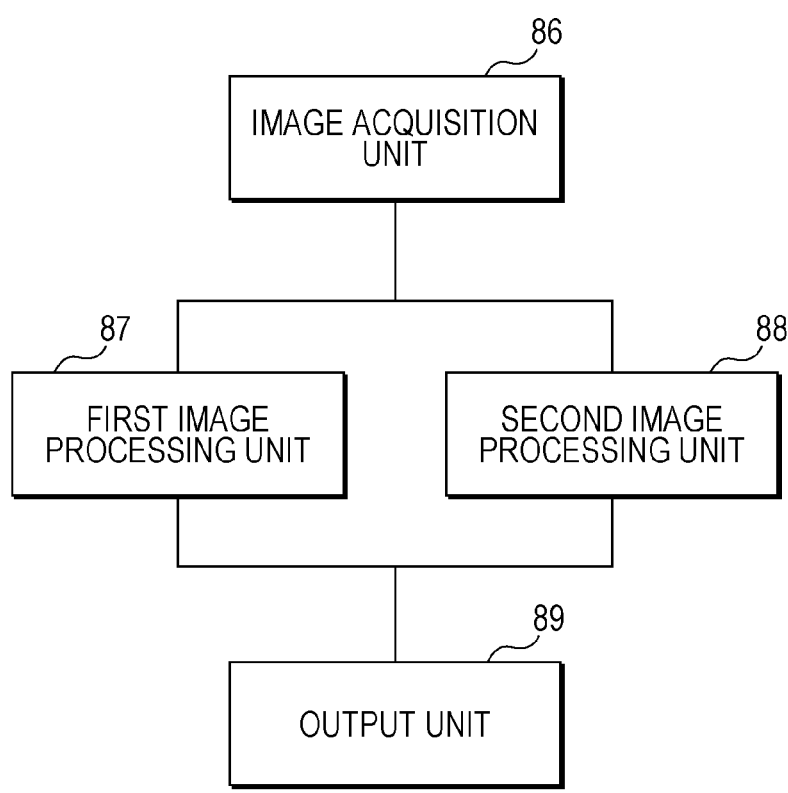
FIG. 26 is a functional block diagram of an endoscope system according to an eighth embodiment.

FIG. 26 is a functional block diagram of the endoscope processor 20 according to the eighth embodiment. The endoscope processor 20 includes an image acquisition unit 86, a first image processing unit 87, a second image processing unit 88, and an output unit 89.

The image acquisition unit 86 acquires a captured image taken by the endoscope 40. The first image processing unit 87 generates the first processed image 571 based on the captured image acquired by the image acquisition unit 86.

The second image processing unit 88 generates the second processed image 572 based on the captured image. When receiving the first processed image 571 generated by the first image processing unit 87 and the second processed image 572 generated by the second image processing unit 88, the output unit 89 outputs the acquired disease status using the learning model 61 which outputs the disease status.

Technical features (constitutional requirements) described in the respective embodiments can be combined with each other, and new technical features can be formed with the combination.

The embodiments disclosed herein are exemplary in all respects, and it should be considered that the embodiments are not restrictive. The scope of the invention is defined not by the above-described meaning but by claims, and intends to include all modifications within meaning and a scope equal to claims.

REFERENCE SIGNS LIST

- 10 endoscope system
- 15 keyboard
- 16 storage shelf
- 20 endoscope processor
- 21 control unit
- 22 main memory device
- 23 auxiliary memory device
- 24 communication unit
- 25 touch panel
- 251 display unit
- 252 input unit
- 26 display device I/F
- 27 input device I/F
- 28 reading portion
- 31 endoscope connector
- 311 electric connector
- 312 optical connector
- 33 light source
- 34 pump
- 35 water supply tank
- 36 air/water supply port
- 40 endoscope
- 43 operation unit
- 431 control button
- 433 bending knob
- 44 insertion portion
- 441 soft portion
- 442 bending section
- 443 distal tip
- 45 bend preventing portion
- 48 scope connector
- 49 universal cord
- 50 display device
- 53 neural network model
- 531 input layer
- 532 intermediate layer
- 533 output layer
- 56 original image
- 57 processed image
- 571 first processed image
- 572 second processed image
- 573 third processed image
- 574 fourth processed image
- 58 interest region image
- 581 first interest region
- 582 second interest region
- 59 endoscope image
- 61 learning model
- 611 first learning model
- 612 second learning model
- 65 training data DB
- 66 learning model DB
- 71 set selection button
- 72 result field
- 721 first result field
- 722 second result field
- 73 interest part field
- 74 score field
- 754 part field
- 755 correct answer input field
- 756 next button
- 76 examination target part field
- 77 detection target disease field
- 771 ulcer button
- 772 tumor button
- 773 bleeding button
- 774 polyp button
- 78 image processing selection button
- 79 image processing selection field
- 80 server
- 81 control unit
- 82 main memory device
- 83 auxiliary memory device
- 84 communication unit
- 86 image acquisition unit
- 87 first image processing unit
- 88 second image processing unit
- 89 output unit
- 90 computer
- 96 portable recording medium
- 97 program
- 98 semiconductor memory

The invention claimed is:

1. An endoscope processor, comprising:
an image sensor that acquires a captured image taken by an endoscope;
a processor that performs a first image processing operation on the captured image acquired by the image sensor to generate a first processed image,
the processor also performing a second image processing operation on the captured image to generate a second processed image that is different from the first processed image; and
a display that outputs an acquired disease status using a learning model, which outputs a disease status, when the first processed image generated by the processor and the second processed image generated by the processor are input.

2. The endoscope processor according to claim 1, wherein the processor generates an image in which any one of an R component, a G component, and a B component of the captured image is emphasized more than the other components.

3. The endoscope processor according to claim 1, wherein the processor generates an image in which any one of an R component, a G component, and a B component of the captured image is extracted.

4. The endoscope processor according to claim 1, wherein the processor generates an image in which any one of an R component, a G component, and a B component of the captured image is deleted.

5. The endoscope processor according to claim 1, wherein the processor generates an image in which an edge component of the captured image is emphasized.

6. The endoscope processor according to claim 1, wherein
the processor accepts a selection of a learning model to be used from among a plurality of the learning models which output results different from each other,
wherein the display outputs a result of using a learning model that the learning model selection accepting unit has accepted the selection.

7. The endoscope processor according to claim 1, wherein
the processor generates processed images different from each other based on the captured image, image; and
the processor accepts a selection of one of the processed images, and
the display outputs a disease status acquired by using a learning model that outputs the disease status when the processed image corresponding to the accepted selection is input.

8. The endoscope processor according to claim 1,
wherein the display outputs an endoscope image generated based on the captured image together with the disease status.

9. The endoscope processor according to claim 8,
wherein the endoscope image is the first processed image or the second processed image.

10. The endoscope processor according to claim 1, wherein
the processor extracts a portion affecting the output of the learning model from the first processed image and the second processed image,
wherein the display outputs an index indicating a region that is extracted by the processor.

11. The endoscope processor according to claim 1, wherein the processor is configured to generate the first and second processed images by performing different combinations of R component emphasis, G component emphasis, B component emphasis, R component extraction, G component extraction, B component extraction, R component removal, G component removal, B component removal, edge emphasis, normal image processing, and edge emphasis after R component emphasis on the captured image.

12. The endoscope processor according to claim 11, wherein the processor is configured to generate the first and second processed images by performing different combinations of nine or fewer of R component emphasis, G component emphasis, B component emphasis, R component extraction, G component extraction, B component extraction, R component removal, G component removal, B component removal, edge emphasis, normal image processing, and edge emphasis after R component emphasis on the captured image.

13. The endoscope processor according to claim 1, wherein the processor is configured to perform R component emphasis, G component emphasis, B component emphasis, R component extraction, G component extraction, B component extraction, R component removal, G component removal, B component removal, edge emphasis, normal image processing, and edge emphasis after R component emphasis on the captured image.

14. The endoscope processor according to claim 1, wherein the display is configured to display a screen displaying separate user-input areas for inputting the following processes on the captured image: R component emphasis, G component emphasis, B component emphasis, R component extraction, G component extraction, B component extraction, R component removal, G component removal, B component removal, edge emphasis, normal image processing, and edge emphasis after R component emphasis.

15. The endoscope processor according to claim 14, wherein the display accepts inputs from plural user-input areas of the display screen to perform multiple image processing operations on the captured image corresponding to the user-selected user-input areas to generate the first or second processed image so that the processor generates the first or second processed image by performing multiple image processing operations on the captured image input by the user on the user-input areas of the display screen.

16. The endoscope processor according to claim 14, wherein
the display screen also displays a user-selectable examination target part field, a user-selectable detection target disease field, and at least one user-selectable set selection button, and
the learning model outputs a desired disease status based on
an examination target part inputted by the user via the examination target part field,
a detection target disease input by the user via the selectable detection target disease field, and
a combination of image processing operations input by the user via a combination of user-input areas for inputting R component emphasis, G component emphasis, B component emphasis, R component extraction, G component extraction, B component extraction, R component removal, G component removal, B component removal, edge emphasis, normal image processing, and edge emphasis after R component emphasis.

17. The endoscope processor according to claim 14, wherein the display screen also displays
i) an image showing an image of the interest region based on the captured image, and
ii) plural probabilities based on the learning model, comprising the probabilities that the displayed interest region has
a severe ulcer, a moderate ulcer, a mild ulcer, and no ulcer, or
a malignant tumor, a benign tumor, and no tumor.

18. An information processing device, comprising:
an image sensor that acquires a captured image taken by an endoscope from an endoscope processor;
a processor that performs a first image processing operation on the captured image acquired by the image sensor to generate a first processed image,
wherein the processor also performs a second image processing operation on the captured image to generate a second processed image that is different from the first processed image; and
a display that outputs an acquired disease status using a learning model, which outputs a disease status, when the first processed image generated by the processor and the second processed image generated by the processor unit are input.

19. A non-transitory computer-readable medium including a program for causing a computer to execute:
acquiring a captured image taken by an image sensor of an endoscope;
performing a first image processing operation on the captured image acquired by the image sensor to generate a first processed image with a processor;
performing a second image processing operation on the captured image acquired by the image sensor to generate a second processed image that is different from the first processed image with the processor; and outputting with a display, when the first processed image and the second processed image are input, a disease status using a learning model that outputs the disease status.

* * * * *